US008987294B2

(12) United States Patent
Ginsberg et al.

(10) Patent No.: US 8,987,294 B2
(45) Date of Patent: Mar. 24, 2015

(54) SMALL MOLECULE INHIBITORS OF THE α4-PAXILLIN INTERACTION

(75) Inventors: Mark Ginsberg, San Diego, CA (US); Christiane Kummer, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 331 days.

(21) Appl. No.: 13/496,095

(22) PCT Filed: Sep. 15, 2010

(86) PCT No.: PCT/US2010/048897
§ 371 (c)(1),
(2), (4) Date: May 8, 2012

(87) PCT Pub. No.: WO2011/034896
PCT Pub. Date: Mar. 24, 2011

(65) Prior Publication Data
US 2012/0245194 A1    Sep. 27, 2012

Related U.S. Application Data

(60) Provisional application No. 61/243,638, filed on Sep. 18, 2009.

(51) Int. Cl.
*A61K 31/435*    (2006.01)
*C07D 221/06*    (2006.01)
*A61K 31/4375*   (2006.01)

(52) U.S. Cl.
CPC .......... *A61K 31/4375* (2013.01); *C07D 221/06* (2013.01)
USPC ............................................. 514/290; 546/79

(58) Field of Classification Search
CPC .................................................... C07D 221/06
USPC ............................................ 514/290; 546/79
See application file for complete search history.

(56) References Cited

U.S. PATENT DOCUMENTS

2006/0167271 A1    7/2006    Ginsberg et al.

FOREIGN PATENT DOCUMENTS

WO    WO2011034896 A3    10/2011

OTHER PUBLICATIONS

Alon, R., et al., 2005, "Alpha4Beta1-dependent adhesion strengthening under mechanical strain is regulated by paxillin association with the alpha4-cytoplasmic domain," J.Cell Biol.2005,171:pp. 1073-1084. 2005 The Rockefeller University Press.
Ambroise, Yves et al., 2002, "Inhibitors of Cell Migration that Inhibit Intracellular Paxillin/alpha4 Binding: A Well-Documented Use of Positional Scanning Libraries,Chemistry & Biology," pp. 1219-1226, vol. 9, Issue 11, Elsevier Science Ltd.
Feral, Chloe C. et al., 2006, "Blocking the alpha4 integrin-paxillin interaction selectively impairs mononuclear leukocyte recruitment to an inflammatory site," The Journal of Clinical Investigation, 116 (3) published as Research Article, The Journal of Clinical Investigation, pp. 1-9, http://www.jci.org.
Feral, C.C., et al., 2006, "Blocking the alpha.4 integrin-paxillin interaction selectively impairs mononuclear leukocyte recruitment to an inflammatory site," J Clin. Invest 116: 715-723.
Hyduk, S.J., et al., 2004, "Paxillin selectively associates with constitutive and chemoattractant-induced high-affinity alpha4beta1 integrins: implications for integrin signaling," Blood 104:2818-2824. bloodjournal.hematologylibrary.org.
Liu, S., et al., 1999, "Binding of Paxillin binding to alpha 4 integrins modifies integrin-dependent biological responses," Nature 402: pp. 676-681.
Liu, Shouchun et al., 2000, "Paxillin binding to a Conserved Sequence Motif in the alpha 4 Integrin Cytoplasmic Domain," J Biol Chem 275, 22736-22742, http://www.jbc.org/content/275/30/22736.long.
Liu, S. et al., 2002, "A fragment of Paxillin binds the alpha 4 integrin cytoplasmic domain (Tail) and selectively inhibits alpha 4-mediated cell migration," J.Biol.Chem. 277:20887-20894.Epub 2002, http://www.jbc.org/content/277/23/20887.long.
Nishiya, Naoyuki et al., 2005, "An alpha4 integrin-paxillin-Art-GAP complex restricts Rac activation to the leading edge of migrating cells," Nat. Cell Biol. 7, 343-352, 2005 Nature Publishing Group.
Rose, David M., et al., 2003, "Paxillin Binding to the Alpha4 integrin subunit stimulates LFA-1 (Integrin AlphaL Beta2)-Dependent T Cell Migration by Augmenting the Activation of Focal Adhesion Kinase/Proline-Rich Tyrosine Kinase-2," J Immunol 170:5912-5918, by The American Association of Immunologists, Inc.
von Andrian, Ulrich H. et al., 2003, "Alpha4 integrins as therapeutic targets in autoimmune disease," N.Engl.J Med. 348:68-72, www.nejm.org.
Young, B.A. et al., 2001, "The cytoplasmic domain of the integrin alpha9 subunit requires the adaptor protein paxillin to inhibit cell spreading but promotes cell migration in a paxillin-independent manner," Mol.Biol Cell 12:3214-3225, by the American Society for Cell Biology.

*Primary Examiner* — Rita Desai
(74) *Attorney, Agent, or Firm* — Sutherland Asbill & Brennan LLP

(57) ABSTRACT

The present invention is directed to novel compounds that are able to inhibit the interaction of paxillin or its paralogues, including leupaxin or Hic-5, with alpha.4 integrin or its binding partners that regulate signaling events downstream of the paxillin-.alpha.4 interaction. The present invention further relates to methods for therapeutic use of such compounds and pharmaceutical compositions of such compounds for the treatment of a disease or condition.

9 Claims, 11 Drawing Sheets

SMALL MOLECULE INHIBITORS OF THE α4-PAXILLIN INTERACTION

CROSS REFERENCES

This application is a US national stage entry of PCT Application No. PCT/US2010/048897 filed Sep. 15, 2010, which claims priority to U.S. Provisional patent application Ser. No. 61/243,638 filed on Sep. 18, 2009, both of which are incorporated herein by reference in their entirety.

STATEMENT REGARDING FEDERALLY SPONSORED RESEARCH

This invention was made with government support under Grant No: AR27214, NS059433, and AR52367 awarded by the National Institutes of Health. The government has certain rights in the invention.

FIELD OF THE INVENTION

The present invention is directed to novel compounds that are able to inhibit the interaction of paxillin or its paralogues, including leupaxin or Hic-5, with α4 integrin or its binding partners that regulate signaling events downstream of the paxillin-α4 interaction. The present invention further relates to methods for therapeutic use of such compounds.

BACKGROUND OF THE INVENTION

α4 integrins are prominent on mononuclear leukocytes. They mediate cell migration, which is dependent on binding of the intracellular adaptor protein paxillin to the cytoplasmic tail of α4.

α4 integrin antagonists are effective in inhibiting a wide variety of experimental models of inflammatory diseases(1-4) and autoimmunity because they inhibit the recruitment of lymphocytes and monocytes to sites of inflammation. Furthermore, anti-α4 antibodies are of proven therapeutic effectiveness in human autoimmune diseases, such as Multiple Sclerosis(5). Anti-α4 antibodies, such as natalizumab, and small molecule and peptidomimetic α4 antagonists inhibit the integrin's interactions with ligands such as VCAM-1. At saturation, this form of inhibition causes complete loss of α4 integrin function. Consequently, use of these agents recapitulates the null phenotype implying the potential for mechanism-based toxicities such as defects in placentation, heart development, and hematopoiesis(6). Furthermore, the blockade of T cell entry into the central nervous system accounts for the occurrence of Progressive Multifocal Leukoencephalopathy in humans treated with anti-α4 integrin antibodies (7).

Integrin functions depend on their capacity to generate and respond to cellular signals. Blockade of integrin signaling can leave ligand binding function intact(8-10). Consequently, only partial inhibition of function may occur, even with full blockade of the target, potentially providing a more favorable therapeutic window. A quest for interactions important in α4 integrin signaling uncovered a tight binding interaction of the α4 cytoplasmic domain with paxillin, a signaling adaptor (11). Blocking the interaction by mutations of α4 (e.g. α4(Y991A)) that selectively block paxillin binding, reduces cell migration(10;11).

Furthermore, inhibition of paxillin binding to α4 by a fragment of paxillin(12) or a small molecule antagonist(13) also impairs migration, suggesting that such agents could be used as therapeutic inhibitors of α4 integrin function. Notably, blocking the interaction of α4 with paxillin does not disrupt α4-mediated static adhesion(8;11), suggesting that this form of antagonism might not interfere with functions such as anchorage of hematopoietic progenitors in the bone marrow. Present inventors have previously confirmed this idea by generating mice homozygous for an α4 mutation (α4(Y991A)) that selectively(11) blocks paxillin binding. Similarly, inventors have previously reported that unlike α4 null mice(6;14), these α4(Y991A) mice are viable and fertile; however, they manifest a profound deficit in the recruitment of mononuclear leukocytes to an inflammatory site with no defect in neutrophil recruitment(29). Furthermore, α4 integrins are essential for definitive hematopoiesis(6;15;16); however, the α4(Y991A) mice exhibited normal hemograms, normal abundance of hematopoietic precursors and unimpaired homing of hematopoietic progenitor cells to the bone marrow, a surrogate marker of stem cell migration. Thus inventors have previously established the principle that blockade of α4 integrin signaling can impair mononuclear leukocyte recruitment to an inflammatory site, while averting the adverse effects of α4 integrin loss on development and hematopoiesis (29).

While existing antagonists of the α4 integrin are useful as therapeutic agents for autoimmune diseases, they are also associated with a number of serious toxic side effects. Specifically, known antagonists of the α4 integrin can affect development and hematopoiesis, and are also associated with progressive multifocal leukoencephalopathy.

The present invention describes novel compounds that are able to inhibit the interaction of paxillin or its paralogues with α4 integrin or its binding partners that regulate signaling events downstream of the paxillin-α4 interaction and methods for therapeutic use of such compounds. The compounds of the present invention are able to inhibit the interaction of paxillin or its paralogues with α4 integrin or its binding partners without resulting in hematopoietic or developmental toxicities.

SUMMARY OF THE INVENTION

The present inventipn generally describes novel compounds that are able to inhibit the interaction of paxillin or its paralogues with α4 integrin or binding partners that regulate signaling events downstream of the paxillin-α4 interaction.

In one embodiment, the present invention describes novel compounds that are able to inhibit the interaction of paxillin or its paralogues, including leupaxin or Hic-5, with α4 integrin or binding partners that regulate signaling events downstream of the paxillin-α4 integrin interaction.

In another embodiment, the present invention describes methods for therapeutic use of compounds that are able to inhibit the interaction of paxillin or its paralogues, including leupaxin or Hic-5, with α4 integrin or binding partners that regulate signaling events downstream of the paxillin-α4 integrin interaction.

These and various other advantages and novel features characterizing the present invention are also particularly pointed out in the claims attached to and forming a part of the present application. However, for a better understanding of the invention, its advantages, and objectives obtained by its use, reference should also be made to the accompanying descriptive disclosure, in which the preferred embodiments and methods of practicing the present invention are described in requisite detail.

BRIEF DESCRIPTION OF THE DRAWINGS

FIG. 1A depicts a schematic of the ELISA assay performed for High throughput screening. Biotinylated recombinant α4- or αIIb tails were immobilized on neutravidin coated 384-well plates (1). Bound proteins were incubated with HA-tagged recombinant leupaxin or paxillin in the presence or absence (control) of library compounds (2). Bound leupaxin or paxillin was detected by incubation with an anti HA-tag antibody (3) followed by HRP-conjugate (4) and detected by luminescence (5). FIG. 1B depicts a schematic of 6×His-recombinant integrin cytoplasmic tail model proteins. α4 and αIIb proteins were modified by inserting a sequence encoding the peptide, GLNDIFEAQKIEWHE. FIG. 1C depicts a summary of screening results.

FIG. 11A, images, paxillin localization in VEGF-C stimulated WT and α4Y991A LECs; graph, VEGF-C stimulated WT and α4Y991A LEC cell migration. FIG. 11B, left, mean area of microvessel sprouting from WT or α4Y991A thoracic duct explants (n=6; *, $P<0.04$); right, bright field images of explants. FIG. 11C, mean Lyve-1+ pixels per field±SEM in saline and VEGF-C saturated Matrigel implanted in WT and α4Y991A mice(*, $P<0.001$).

DETAILED DESCRIPTION OF THE INVENTION

Figure 1:
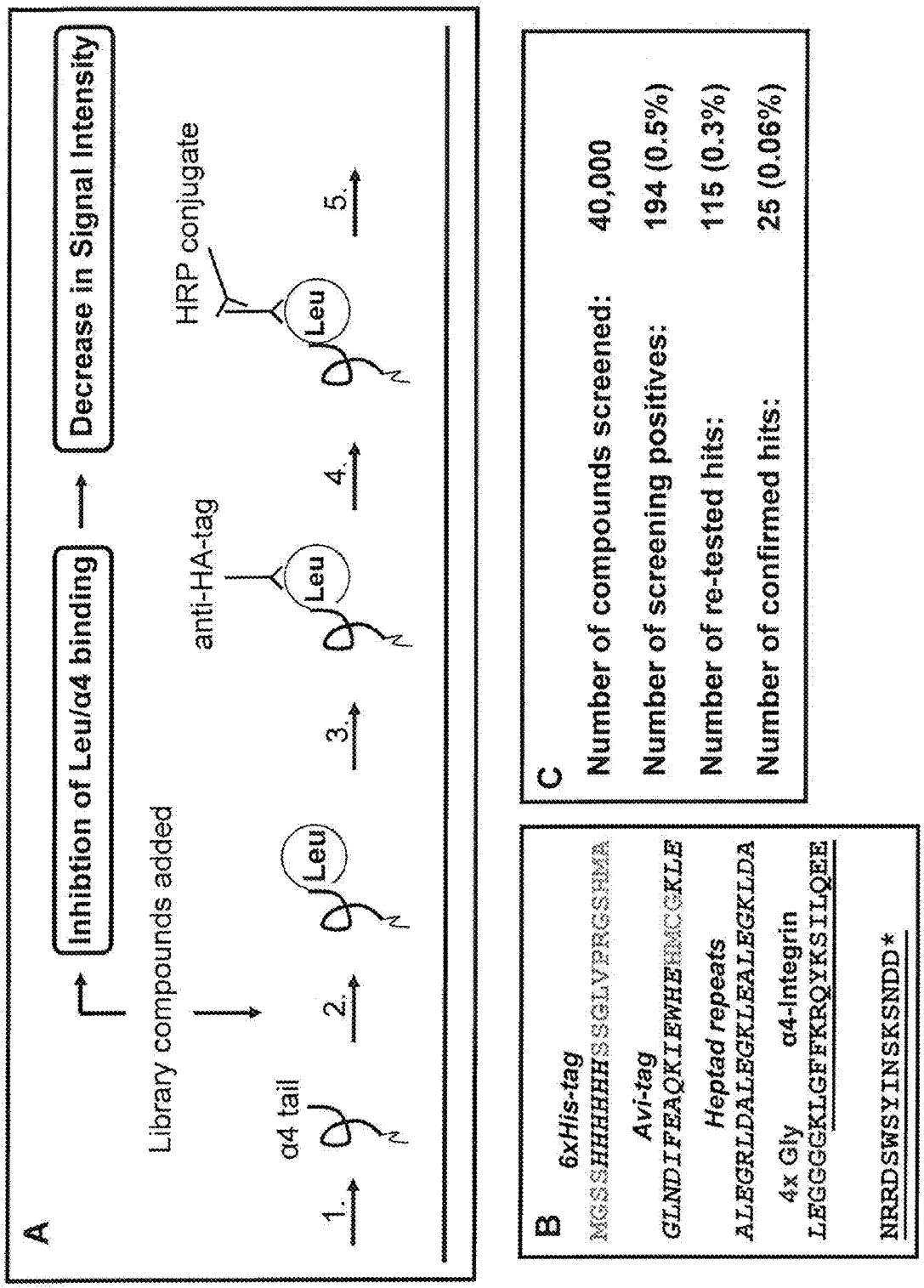

The present invention is based upon the discovery of certain novel compounds that are able to inhibit the interaction of paxillin or its paralogues, including leupaxin or Hic-5, with α4 integrin or binding partners that regulate signaling events downstream of the paxillin-α4 integrin interaction. These novel compounds are able to interfere with α4 integrin signaling and thus selectively impair mononuclear leukocyte recruitment to sites of inflammation while eliminating hematopoietic or developmental toxicities.

Unless defined otherwise, all technical and scientific terms used herein have the same meaning as is commonly understood by one of skill in the art to which this invention belongs.

In accordance with the present invention and as used herein, the following terms are provided for nomenclature purposes. Furthermore, in an effort to maintain consistency in the naming of compounds of similar structures but differing substituents, the compounds described herein are named according to the following general guidelines.

The terms alkyl, alkenyl and alkynyl include straight-chain, branched-chain, saturated and/or unsaturated structures, and combinations thereof.

The terms heteroalkyl, heteroalkenyl and heteroalkynyl include optionally substituted $C_1$-$C_{10}$ alkyl, alkenyl and alkynyl structures, as described above, in which one or more skeletal atoms is oxygen, nitrogen, sulfur, or combinations thereof.

The terms haloalkyl, haloalkenyl and haloalkynyl include $C_1$-$C_{10}$ alkyl, alkenyl and alkynyl structures, as described above, that are substituted with one or more fluorines, chlorines, bromines or iodines, or with combinations thereof.

The terms cycloalkyl and cycloalkene include optionally substituted, saturated and/or unsaturated $C_3$-$C_7$ carbocyclic structures.

The term heterocycle or analogous term such as heterocyclic includes optionally substituted, saturated and/or unsaturated, three- to seven-membered cyclic structures in which one or more skeletal atoms are oxygen, nitrogen, sulfur, or combinations thereof.

The term aryl refers to optionally substituted six-membered aromatic rings including optionally substituted polycyclic carbon ring systems of two to four, more preferably two to three, and most preferably two rings, including, without limitation, phenyl, biphenyl, naphthyl and anthryl ring systems.

The term heteroaryl refers to optionally substituted five- or six-membered heterocyclic aromatic rings containing one or more heteroatoms. The heterocyclic rings may contain one or more heteroatoms selected from the group consisting of oxygen, nitrogen and sulfur and six-membered heterocyclic rings may contain one or more nitrogens. Heterocyclic rings include polycyclic ring systems of from two to four, more preferably two to three, and most preferably two aromatic rings including, without limitation, furyl, pyrrolyl, pyrrolidinyl, thienyl, pyridyl, piperidyl, indolyl, quinolyl, thiazole, benzthiazole and triazole.

The term acyl includes alkyl, aryl, heteroaryl, arylalkyl or heteroarylalkyl substituents attached to a compound via a carbonyl functionality (e.g., —CO-alkyl, —CO-aryl, —CO-arylalkyl or heteroarylalkyl etc. . . . ).

The substituents of an "optionally substituted" structure may include, but are not limited to, one or more of the following preferred substituents: F, Cl, Br, I, CN, $NO_2$, $NH_2$, $NHCH_3$, $N(CH_3)_2$, SH, $SCH_3$, OH, $OCH_3$, $OCF_3$, $CH_3$, $CF_3$.

As used herein, the term "nucleic acid," "nucleic acid sequence," "polynucleotide," or similar terms, refers to a deoxyribonucleotide or ribonucleotide, oligonucleotide or polynucleotide, including single- or double-stranded forms, and coding or non-coding (e.g., "antisense") forms. The term encompasses nucleic acids containing known analogues of natural nucleotides. The term also encompasses nucleic acids including modified or substituted bases as long as the modified or substituted bases interfere neither with the Watson-Crick binding of complementary nucleotides or with the binding of the nucleotide sequence by proteins that bind specifically, such as zinc finger proteins. The term also encompasses nucleic-acid-like structures with synthetic backbones. DNA backbone analogues provided by the invention include phosphodiester, phosphorothioate; phosphorodithioate, methylphosphonate, phosphoramidate, alkyl phosphotriester, sulfamate, 3'-thioacetal, methylene(methylimino), 3'-N-carbamate; morpholino carbamate, and peptide nucleic acids (PNAs); see Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) J. Med. Chem. 36:1923-1937; Antisense Research and Applications (1993, CRC Press). PNAs contain non-ionic backbones, such as N-(2-aminoethyl)glycine units. Phosphorothioate linkages are described, e.g., by U.S. Pat. Nos. 6,031, 092; 6,001,982; 5,684,148; see also, WO 97/03211; WO 96/39154; Mata (1997) Toxicol. Appl. Pharmacol. 144:189-197. Other synthetic backbones encompassed by the term include methylphosphonate linkages or alternating methylphosphonate and phosphodiester linkages (see, e.g., U.S. Pat. No. 5,962,674; Strauss-Soukup (1997) Biochemistry 36:8692-8698), and benzylphosphonate linkages (see, e.g., U.S. Pat. No. 5,532,226; Samstag (1996) Antisense Nucleic Acid Drug Dev 6:153-156). Such analogues can be employed in the preparation and use of antisense nucleic acids as is well known in the art, such as for the purpose of inhibiting transcription. Additionally, the recitation of a nucleic acid sequence includes its complement unless the complement is specifically excluded or the context makes it clear that only one strand of the nucleic acid sequence is intended to be utilized. Additionally, the recitation of a nucleic acid sequence includes DNA, RNA, or DNA-RNA hybrids unless the context makes it clear that only one specific form of the nucleic acid sequence is intended to be utilized.

As used herein, the amino acids, which occur in the various amino acid sequences appearing herein, are identified according to their well-known, three-letter or one-letter abbreviations. The nucleotides, which occur in the various DNA fragments, are designated with the standard single-letter designations used routinely in the art.

In a peptide or protein, suitable conservative substitutions of amino acids are known to those of skill in this art and may be made generally without altering the bioiogical activity of the resulting molecule. Those of skill in this art recognize that, in general, single amino acid substitutions in non-essentiial regions of a polypeptide do not substantially alter biological activity (see, e.g. J. D. Watson et al., "Molecular Biology of the Gene" (4th Edition, 1987, Bejamin/Cummings, Palo Alto), p. 224). Specifically, in particular, the conservative amino acid substitutions can be any of the following: (1) any of isoleucine for leucine or valine, leucine for isoleucine, and valine for leucine or isoleucine; (2) aspartic acid for glutamic acid and glutamic acid for aspartic acid; (3) glutamine for asparagine and asparagine for glutamine; and (4) serine for threonine and threonine for serine. Other substitutions can also be considered conservative, depending upon the environment of the particular amino acid. For example, glycine (G) and alanine (A) can frequently be interchangeable, as can be alanine and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the different pK's of these two amino acid residues or their different sizes are not significant. Still other changes can be considered "conservative" in particular environments. For example, if an amino acid on the surface of a protein is not involved in a hydrogen bond or salt bridge interaction with another molecule, such as another protein subunit or a ligand bound by the protein, negatively charged amino acids such as glutamic acid and aspartic acid can be substituted for by positively charged amino acids such as lysine or arginine and vice versa. Histidine (H), which is more weakly basic than arginine or lysine, and is partially charged at neutral pH, can sometimes be substituted for these more basic amino acids. Additionally, the amides glutamine (Q) and asparagine (N) can sometimes be substituted for their carboxylic acid homologues, glutamic acid and aspartic acid.

As used herein, "expression vector" refers to a plasmid, virus or other vehicle known in the art that has been manipulated by insertion or incorporation of heterologous DNA, such as nucleic acid encoding the fusion proteins herein or expression cassettes provided herein. Such expression vectors contain a promoter sequence for efficient transcription of the inserted nucleic acid in a cell. The expression vector typically contains an origin of replication, and a promoter, as well as specific genes that permit phenotypic selection of transformed cells.

As used herein, "host cells" are cells in which a vector can be propagated and its DNA expressed. The term also includes any progeny of the subject host cell. It is understood that all progeny may not be identical to the parental cell since there may be mutations that occur during replication. Such progeny are included when the term "host cell" is used. Methods of stable transfer where the foreign DNA is continuously maintained in the host are known in the art.

As used herein, an expression or delivery vector refers to any plasmid or virus into which a foreign or heterologous DNA may be inserted for expression in a suitable host Cell—i.e., the protein or polypeptide encoded by the DNA is synthesized in the host cell's system. Vectors capable of directing the expression of DNA segments (genes) encoding one or more proteins are referred to herein, as "expression vectors". Also included are vectors that allow cloning of cDNA (complementary DNA) from mRNAs produced using reverse transcriptase.

As used herein, a gene refers to a nucleic acid molecule whose nucleotide sequence encodes an RNA or polypeptide. A gene can be either RNA or DNA. Genes may include regions preceding and following the coding region (leader and trailer) as well as intervening sequences (introns) between individual coding segments (exons).

As used herein, "isolated," with reference to a nucleic acid molecule or polypeptide or other biomolecule means that the nucleic acid or polypeptide has separated from the genetic environment from which the polypeptide or nucleic acid were obtained. It may also mean altered from the natural state. For example, a polynucleotide or a polypeptide naturally present in a living animal is not "isolated", but the same polynucleotide or polypeptide separated from the coexisting materials of its natural state is "isolated", as the term is employed herein. Thus, a polypeptide or polynucleotide produced and/or contained within a recombinant host cell is considered isolated. Also intended as an "isolated polypeptide" or an "isolated polynucleotide" are polypeptides or polynucleotides that have been purified, partially or substantially, from a recombinant host cell or from a native source. For example, a recombinantly produced version of a compound can be substantially purified by the one-step method described in Smith et al. (1988) Gene 67:3140. The terms isolated and purified are sometimes used interchangeably.

Thus, by "isolated" the nucleic acid is free of the coding sequences of those genes that, in a naturally-occurring genome immediately flank the gene encoding the nucleic acid of interest. Isolated DNA may be single-stranded or double-stranded, and may be genomic DNA, cDNA, recombinant hybrid DNA, or synthetic DNA. It may be identical to a native DNA sequence, or may differ from such sequence by the deletion, addition, or substitution of one or more nucleotides.

Isolated or purified as it refers to preparations made from biological cells or hosts means any cell extract containing the indicated DNA or protein, including a crude extract of the DNA of protein of interest. For example, in the case of a protein, a purified preparation can be obtained following an individual technique or a series of preparative or biochemical techniques and the DNA or protein of interest can be present at various degrees of purity in these preparations. The procedures may include for example, but are not limited to, ammonium sulfate fractionation, gel filtration, ion exchange chromatography, affinity chromatography, density gradient centrifugatioh, electrophoresis, electrofocusing, chromatofocusihg, of other protein purification techniques known in the art.

A preparation of DNA or protein that is "substantially pure" or "isolated" should be understood to mean a preparation free from naturally occurring materials with which such DNA or protein is normally associated in nature. "Essentially pure" should be understood to mean a "highly" purified preparation that contains at least 95% of the DNA or protein of interest.

As used herein, the term "vector" refers to a nucleic acid molecule capable of transporting between different genetic environments another nucleic acid to which it has been operatively linked. Preferred vectors are those capable of autonomous replication and expression of structural gene products present in the DNA segments to which they are operatively linked. Vectors, therefore, preferably contain the replicons and selectable markers described earlier.

All publications, including but not limited to patents and patent applications, cited in this specification are herein incorporated by reference as though fully set forth in the present application.

While the preferred embodiments of the present invention are illustrated below in numerical order, it is to be understood that the invention is not limited to the precise instructions and embodiments disclosed herein and that the right to all modifications coming within the scope of the following claims is reserved.

One embodiment of the present invention, referred to herein as embodiment 1, is a compound selected from the group consisting of (a) a compound of formula (I);

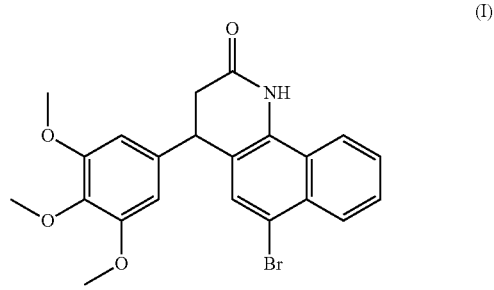 [SMILES: COc1cc(C2CC(=O)Nc3c2cc(Br)c2ccccc32)cc(OC)c1OC]

(b) a prodrug of a compound of formula (I); (c) a salt of a compound of formula (I); and (d) a solvate of a compound of formula (I). The present invention further provides for a small molecule of formula (I) that inhibits the α4-paxillin interaction in vitro. Specificity was evidenced by an almost identical structure (one methoxy group is shifted from position 5 to 2) having no inhibitory effect on the interaction.

In the case of salts, it is well known that organic compounds, including compounds having activities suitable for methods according to the present invention, have multiple groups that can accept or donate protons, depending upon the pH of the solution in which they are present. These groups include carboxyl groups, hydroxyl groups, amino groups, sulfonic acid groups, and other groups known to be involved in acid-base reactions. The recitation of a compound or analogue includes such salt forms as occur at physiological pH or at the pH of a pharmaceutical composition unless specifically excluded.

Similarly, prodrug esters can be formed by reaction of either a carboxyl or a hydroxyl group on compounds or analogues suitable for methods according to the present invention with either an acid or an alcohol to form an ester. Typically, the acid or alcohol includes a lower alkyl group such as methyl, ethyl, propyl, isopropyl, butyl, isobutyl, and tertiary butyl. These groups can be substituted with substituents such as hydroxy, or other substituents. Such prodrugs are well known in the art and need not be described further here. The prodrug is converted into the active compound by hydrolysis of the ester linkage, typically by intracellular enzymes. Other suitable groups that can be used to form prodrug esters are well known in the art. For example prodrugs can include amides prepared by reaction of the parent acid compound with a suitable amine. In some cases it is desirable to prepare double ester type prodrugs such as (acyloxy)alkyl esters or ((alkoxycarbonyl)oxy)alkyl esters.

Suitable esters as prodrugs include, but are not necessarily limited to, methyl, ethyl, propyl, isopropyl, n-butyl, isobutyl, tert-butyl, morpholinoethyl, and N,N-diethylglycolamido. Methyl ester prodrugs may be prepared by reaction of the acid form of a compound having a suitable carboxylic acid group in a medium such as methanol with an acid or base esterification catalyst (e.g., NaOH, $H_2 SO_4$). Ethyl ester prodrugs are prepared in similar fashion using ethanol in place of methanol. Morpholinylethyl ester prodrugs may be prepared by reaction of the sodium salt of a suitable compound (in a medium such as dimethylformamide) with 4-(2-chloroethyl) morphine hydrochloride (available from Aldrich Chemical Co., Milwaukee, Wis. USA.

Pharmaceutically acceptable salts include acid salts such as hydrochloride, hydrobromide, hydroiodide, sulfate, phosphate, fumarate, maleate, acetates, citrates, lactates, tartrates, sulfamates, malonate, succinate, tartrate, methanesulfonates, ethanesulfonates, benzenesulfonates, p-toluenesulfonates, cyclohexylsulfamates, quinates, formates, cinnamates, picrates, and other suitable salts. Such salts can be derived using acids such as hydrochloric acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, and quinic acid.

Pharmaceutically acceptable salts also include salts with bases such as alkali metal salts such as sodium or potassium, as well as pyridine salts, ammonium salts, piperazine salts, diethylamine salts, nicotinamide salts, calcium salts, magnesium salts, zinc salts, lithium salts, methylamino salts, triethylamino salts, dimethylamino salts, and tris(hydroxymethyl)aminomethane salts.

Another embodiment of the present invention, referred to herein as embodiment 2, is the compound of embodiment 1 wherein the compound is a compound of formula (I).

Another embodiment of the present invention, referred to herein as embodiment 3, is the compound of embodiment 1 wherein the compound is a prodrug of a compound of formula (I).

Another embodiment of the present invention, referred to herein as embodiment 4, is the compound of embodiment 1 wherein the compound is a salt of a compound of formula (I).

Another embodiment of the present invention, referred to herein as embodiment 5, is the compound of embodiment 1 wherein the compound is a solvate of a compound of formula (I).

Another embodiment of the present invention, referred to herein as embodiment 6, is a pharmaceutical composition for the treatment of an immune mediated disease, comprising a therapeutically effective amount of a compound of formula (I) or a pharmaceutically acceptable salt, prodrug or solvate thereof.

Pharmaceutical compositions according to the present invention can be formulated for oral administration or for parenteral administration. The route of administration depends on the chemical nature of the active species, the condition of the patient, and pharmacokinetic considerations such as liver or kidney function.

An additional aspect of the present invention is a method of treating a disease or condition treatable by inhibiting the α4 integrin-paxillin interaction comprising administering a quantity of a compound as described above or subsequently, or of a pharmaceutical composition as described above or subsequently, sufficient to inhibit the interaction of paxillin or its paralogues with α4 integrin or binding partners that regulate signaling events downstream of the paxillin-α4 interaction, thus treating the disease or condition. The disease or condition can be an immune mediated disease or condition. The disease or condition can further include, but is hot limited to, multiple sclerosis, asthma, inflammatory bowel disease, rheumatoid arthritis, diabetes mellitus type I, systemic lupus erythematosus, Crohn's disease, vasculitis, familial Mediterranean fever, Behcet's disease, celiac disease, acute disseminated encephalomyelitis, Addison's disease, ankylosing spondylitisis, aplastic anemia, autoimmune hepatitis, Graves' disease, Guillain-Barre syndrome, and Hashimoto's disease. However, the treatment of other, forms of autoimmune and immune mediated diseases is contemplated by the present invention.

Another embodiment of the present invention, referred to herein as embodiment 7, is the pharmaceutical composition of embodiment 6 wherein the immune mediated disease is selected from the group consisting of multiple sclerosis, asthma, inflammatory bowel disease, rheumatoid arthritis, diabetes mellitus type I, systemic lupus erythematosus, Crohn's disease, vasculitis, familial Mediterranean fever, Behcet's disease, celiac disease, acute disseminated encephalomyelitis, Addison's disease, ankylosing spondylitisis, aplastic anemia, autoimmune hepatitis. Graves' disease, Guillain-Barre syndrome, and Hashimoto's disease.

Another embodiment of the present invention, referred to herein as embodiment 8, is a method for treating an immune mediated disease in a patient, which comprises administering a therapeutically effective amount of a compound of formula I or a pharmaceutically acceptable salt, prodrug or solvate thereof.

Another embodiment of the present invention, referred to herein as embodiment 9, is the method of embodiment 8 wherein the patient is selected from the group consisting of human, mammal, avian, fish and reptile species.

Another embodiment of the present invention, referred to herein as embodiment 10, is the method of embodiment 9 wherein the patient is human.

Another embodiment of the present invention, referred to herein as embodiment 11, is the method of embodiment 8 wherein the immune mediated disease is selected from the group consisting of multiple sclerosis, asthma, inflammatory bowel disease, rheumatoid arthritis, diabetes mellitus type I, systemic lupus erythematosus, Crohn's disease, vasculitis, familial Mediterranean fever, Behcet's disease, celiac disease, acute disseminated encephalomyelitis, Addison's disease, ankylosing spondylitisis, aplastic anemia, autoimmune hepatitis, Graves' disease, Guillain-Barre syndrome, and Hashimoto's disease.

Another embodiment of the present invention, referred to herein as embodiment 12, is a method for treating an immune mediated disease in a patient, which comprises administering the pharmaceutical composition of embodiment 6 to a patient.

Another embodiment of the present invention, referred to herein as embodiment 13, is the method of embodiment 12 wherein the patient is human.

Another embodiment of the present invention, referred to herein as embodiment 14, is a method for inhibiting the interaction of paxillin or its paralogues with α4 integrin or binding partners that regulate signaling events downstream of the paxillin-α4 interaction, comprising administering a therapeutically effective amount of a compound of formula (I) or a pharmaceutically acceptable salt, prodrug or solvate thereof.

Another embodiment of the present invention, referred to herein as embodiment 15, is the method of embodiment 14 wherein the paralogues of paxillin are further selected from the group consisting of leupaxin and Hic-5.

The compounds of the present invention may contain one or more chiral centers, and may exist in different optically active forms. When compounds of the present invention contain one chiral center, the compounds exist in two enantiomeric forms and the present invention includes both enantiomers and mixtures of enantiomers, such as racemic mixtures.

The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent.

It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound of the present invention has one or more chiral substituents it may exist in diastereoisomeric forms. The diastereoisomeric pairs may be separated by methods known to those skilled in the art, for example chromatography or crystallization and the individual enantiomers within each pair may be separated as described above. The present invention includes each diastereoisomer of compounds disclosed herein as well as any and all mixtures thereof.

Certain compounds of the present invention may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of the present invention and mixtures thereof.

Certain compounds of the present invention may exist in zwitterionic form and the present invention includes each such zwitterionic form and mixtures thereof.

Certain compounds of the present invention and their salts may exist in more than one crystal form. Polymorphs of compounds of the present invention form part of this invention and may be prepared by crystallization of a compound(s) of the present invention under different conditions.

For example, different conditions which may be potentially used to prepare polymorphs of compounds of the present invention include but are not limited to using different solvents or different solvent mixtures for recrystallization; crystallization at different temperatures; various modes of cooling, ranging from very fast to very slow cooling during crystallization.

Polymorphs may also be obtained by heating or melting a compound(s) of the present invention followed by gradual or fast cooling. The presence of polymorphs may be determined by solid probe NMR spectroscopy, IR spectroscopy, differential scanning calorimetry, powder X-ray diffraction or such other techniques.

The compounds disclosed in the present invention represent a novel group of small molecules that are able to target and kill pancreatic cancer cells in a genotype-selective manner, namely by targeting pancreatic cancer cells with DPC4 gene deficiency.

The particular conditions that can be treated with the compounds of the present invention include but are not limited to various types of autoimmune and immune mediated diseases and disorders, such as multiple sclerosis, asthma, inflammatory bowel disease, rheumatoid arthritis, diabetes mellitus type I, systemic lupus erythematosus, Crohn's disease, vasculitis, familial Mediterranean fever, Behcet's disease, celiac disease, acute disseminated encephalomyelitis, Addison's disease, ankylosing spondylitisis, aplastic anemia, autoimmune hepatitis, Graves' disease, Guillain-Barre syndrome, and Hashimoto's disease.

Furthermore, it is understood by those skilled in the art that the compounds of the present invention, including but not limited to pharmaceutical compositions and formulations containing these compounds can be used in a wide variety of combination therapies to treat the conditions and diseases described above. As described above, all compounds within the scope of the present invention can be used to formulate appropriate pharmaceutical compositions, and such pharmaceutical compositions can be used to treat the conditions described above, including, but not limited to, pancreatic cancer and colon cancer. The use of pharmaceutical compositions according to the present invention is further contemplated for the treatment of other conditions in which it is necessary to block the α4 integrin-paxillin interaction including but not limited to lymphangiogenesis (40), tumor metastasis (40) and selective impairment of mononuclear leukocyte recruitment to an inflammatory site.

Pharmaceutical Formulation and Administration:

Compound(s) of the present invention or derivative(s) and/or combination(s) thereof, as the active ingredient, can be put in pharmaceutically acceptable formulations, such as those described in Remington's Pharmaceutical Sciences, $18^{th}$ ed., Mack Publishing Co., Easton, Pa. (1990), incorporated by reference herein, and used for specific treatment of diseases and pathological conditions with little or no effect on healthy tissues.

The preparation of a pharmacological composition comprising active ingredients dissolved or dispersed therein need not be limited based on formulation. Such compositions may be prepared as injectable liquid solutions or suspensions.

However, solid forms suitable for dissolution, or resuspension, in liquid prior to use can also be prepared. The preparation can also be emulsified.

In a preferred embodiment, the composition is held within a container, which includes a label stating to the effect that the composition is approved by the FDA in the United States (or other equivalent labels in other countries) for treating a disease or condition described herein. Such a container will provide therapeutically effective amount of the active ingredient to be administered to a host.

The particular therapeutic agents that affect the conditions of interest can be administered to a mammal either alone or in pharmaceutical compositions where it is mixed with suitable carrier(s) or excipient(s). In treating a mammal exhibiting a condition of interest, a therapeutically effective amount of an agent or agents, such as one of the structures of the present invention (including, but not limited to compounds of Formula (I) and derivatives thereof), is administered. The active ingredient can be mixed with excipients that are pharmaceutically acceptable and compatible with said active ingredient and in amounts suitable for use in the therapeutic methods described herein.

Pharmaceutically acceptable salts can be prepared by standard techniques. For example, the free base form of the compound is first dissolved in a suitable solvent such as an aqueous or aqueous-alcohol solution, containing the appropriate acid. The salt is then isolated by evaporating the solution. In another example, the salt is prepared by reacting the free base and acid in an organic solvent.

Carriers or excipients can be used to facilitate administration of the compound, for example, to increase the solubility of the compound. Examples of carriers and excipients include calcium carbonate, calcium phosphate, various sugars or types of starch, cellulose derivatives, gelatin, vegetable oils, polyethylene glycols, water, saline, dextrose, glycerol, ethanol and physiologically compatible solvents.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred.

The data obtained from these cell culture assays and animal studies can be used in formulating a range of dosage for use in human. The dosage of such compounds lies preferably within a range of circulating concentrations that include the ED50 with little or no toxicity. The dosage may vary within this range depending upon the dosage form employed and the route of administration utilized.

For any α4 integrin-paxillin interaction inhibitor compound used in the methods of the invention, the therapeutically effective dose can be estimated initially from cell culture assays. For example, a dose can be formulated in animal models to achieve a circulating plasma concentration range that includes the IC50 as determined in cell culture (i.e., the concentration of the test compound which achieves a half-maximal disruption of the protein complex, or a half-maximal inhibition of the cellular level and/or activity of a complex component). Such information can be used to more accurately determine useful doses in humans. Levels in plasma may be measured, for example, by HPLC.

The exact formulation, route of administration and dosage can be chosen by the individual physician in view of the mammal's condition. (See e.g. Fingl et al., in The Pharmacological Basis of Therapeutics, 1975, Ch. 1 p. 1). It should be noted that the attending physician would know how to and when to terminate, interrupt, or adjust administration due to toxicity, or to organ dysfunctions.

Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency will also vary according to the age, body weight, and response of the individual mammal.

Depending on the specific conditions being treated, such agents may be formulated and administered systemically or locally. Techniques for formulation and administration may be found in Remington's Pharmaceutical Sciences, 18th ed., Mack Publishing Co., Easton, Pa. (1990), which is incorporated herein by reference.

For injection, the agents of the invention may be formulated in aqueous solutions, preferably in physiologically compatible buffers such as Hanks's solution, Ringer's solution, or physiological saline buffer.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein. In addition to the active ingredients, these pharmaceutical compositions may contain suitable pharmaceutically acceptable carriers comprising excipients and auxiliaries which facilitate processing of the active compounds into preparations which can be used pharmaceutically. The pharmaceutical compositions of the present invention may be manufactured in a manner that is itself known, e.g., by means of conventional mixing, dissolving, granulating, dragee-making, levitating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions.

Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

EXAMPLES

Experimental Procedures

Cell Lines—
Cell lines (Jurkat T cells, THP-1 cells and Chinese Hamster Ovary (CHO) cells) were obtained from American Type Culture Collection (ATCC). Jurkat cell lines expressing α4 with an alanine substitution at tyrosine 991 (JB4-Y991A cells) were generated as described before (8). Jurkat cell iines were cultured in RPMI1640 (Cellgrow, Mediatech, Washington, D.C.) supplemented with 10% fetal bovine serum (Cellgrow, Mediatech, Washington, D.C.), 1% glutamine, 50 U/ml penicillin, 50 μg/ml streptomycin (Sigma-Aldrich, St. Louis, Mo.) and 1% non-essential amino acids (Gibco by Invitrogen, Carlsbad, Calif.). THP-1 cells were grown in RPMI1640 supplemented with 10% heat-inactivated fetal bovine serum, 10 mM Hepes, 50 μg/ml gentamycin, 50 μM 2-mercaptoethanol, and 50 μg/ml gentamycin. CHO cell lines expressing the α4 subunit or its mutant proteins have been described previously (30, 31). CHO cells were cultured in Dulbecco's modified Eagle's medium supplemented with 10% fetal bovine serum, 1% glutamine, 50 U/ml penicillin, 50 μg/ml streptomycin (Sigma-Aldrich, St. Louis, Mo.) and 1% non-essential amino acids (Gibco by Invitrogen, Carlsbad, Calif.).

Reagents—
The mouse monoclonal HRP-conjugated antibody was purchased from Biosource (AMI4404). The mouse monoclonal anti-hemagglutinin (HA) antibody (12CA5) was produced and purified as previously described (32). Purification of the human CS-1 region of fibronectin fused to GST has been described previously (33), using cDNA which was provided by J. W. Smith (Burnham Institute, La Jolla, Calif.). The cDNA for ICAM was a generous gift from D. L. Simmons (CRF Laboratories, University of Oxford, Oxford, U.K.) and was modified as described before (10).

Generation of Recombinant Proteins—
6×His-recombinant integrin cytoplasmic tail model proteins (α4 and αIIb, FIG. 1B) were cloned into pET15b (Noyagen) (34; 35) and modified by inserting a sequence encoding the peptide, GLNDIFEAQKIEWHE, at the NdeI site immediately downstream of the thrombin cleavage site. This peptide directs incorporation of biotin in vivo upon expression in *Escherichia coli* by biotin ligase (Avidiy, Denver) (36). Proteins were expressed and purified from *E. coli* extracts (35). Recombinant 6×His-FAT, the focal adhesion targeting domain of pp125$^{FAK}$ was generated by PCR and cloned into pET15b (Novagen) between restriction sites BamHI and NdeI, expressed in BL21(DE3)pLysS cells (Novagen) and purified using His-bind resin (Novagen).

To generate recombinant full length paxillin, leupaxin or Git-1 with an N-terminal 6×His-tag and a C-terminal HA-tag, oligonucleotides were generated and used in PCR to create cDNAs encoding the protein with a N-terminal HA-tag. Each PCR product was cloned into pET28c (Novagen; paxillin) or pET15b (Novagen; leupaxin, Hic-5, Git-1) between restriction sites BamHI and NdeI. Proteins were expressed in BL21 (DE3)pLysS Cells (Novagen) and purified using His-bind resin (Novagen). Masses of proteins were assessed by SDS-PAGE and Coomassie staining.

ELISA Assay—
Thermo Electron High Binding 96 or 384 well plates were coated with 1 μg/ml neutravidin (Pierce) in 0.05M NaHCO$_3$ pH 9.5 over night at 4° C. After blocking with 1% heat inactivated BSA in PBS for 1 hour at room temperature, plates were incubated with 1 μg/ml of recombinant αIIb-tail or α4-tail FAT or Git-1 in 1% BSA in PBS for one hour at room temperature. Plates were washed twice with 0.2% Tween in PBS to remove unbound protein and incubated with 10 μg/ml HA-tagged leupaxin or paxillin in 0.2% Tween/1% BSA in PBS in the presence or absence of small molecule compounds (5 mM DMSO stock solutions). DMSO concentration never exceeded 2% (up to 10% DMSO alone was found to have no effect on leupaxin or paxillin binding to α4 or FAT). Plates were washed twice and bound leupaxin or paxillin was detected by incubating with the first antibody (12CA5 ascites, 1:10,000 in 0.2% Tween/1% BSA in PBS) for 1 hour at room temperature and then with the secondary antibody (HPR-conjugated anti mouse, Biosource, 1:1,000 in 0.2% Tween, 1% BSA, PBS for 1 hour at room temperature. Binding was quantified after addition of ECL solution on a Victor luminescence plate reader. 0% inhibition control was measured with leupaxin and no compound and 100% inhibition control (background) was measured with no leupaxin and no compound. Each well was duplicated and percent inhibition was averaged. (FIG. 1A)

Analysis of Inhibition of the α4 Leupaxin Interaction by 6-345TTQ—
Inhibition of the α4 leupaxin interaction was measured using the above described ELISA assay. Biotinylated α4-integrin cytoplasmic tail was coated to the plates and incubated with increasing concentrations of leupaxin in the presence of different concentrations of inhibitor or no inhibitor. The data were fitted to equations for models of competitive, non-competitive, uncompetitive of mixed inhibition using Graph Pad Prism 5.0 to test which model fits the best.

High Throughput Screening—
Screening was performed using the above described ELISA assay that was translated into a 384 well plate format at the ICCB (Institute of Chemistry and Cell Biology) Longwood Screening Facility at Harvard Medical School, Boston, Mass. The following libraries were screened: Mixed Commercials 1, 2 & 4, ChemDiv 1 & 2, Specplus, Maybridge 2 & 3, Peakdale2, Starr Foundation Extracts 1 & 2, Philippines Plant Extracts 2, DDS 2, Biomol ICCB known bioreactives, Bionet 2, Enamine 1, IF Lab 1.

Coimmunoprecipitation and Western Blotting—
For endogenous Coimmunoprecipitation experiments, Jurkat T-cells were washed in ice-cold PBS and incubated in 1.6 mM Sulfo-NHS-Biotin (Pierce, Chemical Co.) for 30 minutes at room temperature. Excess biotin was quenched and washed from the cells with PBS/Glycine. Cell lysates were then prepared with lysis buffer containing 20 mM Tris, pH 7.4, 150 mM NaCl, 10 mM EDTA, 1% Triton X-100, 0.05% Tween 20 and a protease inhibitor cocktail (Roche Diagnostics Corp.). Lysate containing 200 μg total cell protein was immunoprecipitated using 2 μg rabbit anti paxillin (RB-4358). Immunoprecipitated proteins were separated by SDS-PAGE (8% Bis-Tris, denaturating and reducing) and transferred to nitrocellulose membranes. Precipitated, biotinylated proteins were detected using HRP-Streptavidin (1:10,000).

Migration Assay—
Cell migration was assayed in a modified Boyden chamber assay system as described previously (8). For Jurkat T cell migration, transwell (Costar) polycarbonate membranes containing 3-μm pores were coated with 10 μg/ml CS-1, an α4 integrin binding fragment of fibronectin or 20 μg/ml ICAM in 0.1M NaHCO$_3$, pH 8.0 overnight at 4° C. Membranes were blocked with 2% BSA in PBS for 30 minutes at room temperature. 2.0×10$^5$ Jurkat T cells in RPMI 1640 with 10% fetal bovine serum were added to the top chamber. Stromal-derived factor-1α (SDF-1α, R&D Systems, Minneapolis, Minn.) at a final concentration of 15 ng/ml in RPMI 1640 with 10% fetal bovine serum was added to the bottom chamber. Cells were allowed to migrate for 5 hours at 37° C. Cells in the bottom chamber were enumerated with a hemacytometer. Small molecule inhibitors were added to the top and bottom chamber in the indicated concentrations.

THP-1 cells were cultured in RPMI1640 containing 0.1% fetal bovine serum for 16 hours before $1\times10^6$ cells were added to the top chamber of transwells with CS1-coated membranes that contained 5-μm pores and allowed to migrate for 3 hours towards RPMI containing 0.1% fetal bovine serum.

Spreading Assay—

Cell spreading was performed as described (11, 34). Briefly, CHO cells or Jurkat cells resuspended in Dulbecco's modified Eagle's medium or RPMI 1640, respectively, containing 0.5% fetal bovine serum and 0.2% BSA were plated on coverslips coated with 3 μg/ml GST-CS-1 in 12 well plates in the presence or absence of the small molecule inhibitor. After spreading for 45 or 180 minutes at 37° C., respectively, cells were fixed, permeabilized and revealed with rhodamine-conjugated phalloidin. The cell area was measured and analyzed using the ImageJ software. At least three independent experiments were performed and in each experiment at least 30 cells were analyzed.

Cytotoxicity Assay—

The cytotoxicity effect of compounds on cultivated cells was determined using the CellTiter 96® Aqueous One Solution Cell Proliferation Assay (Promega, Madison, Wis.) according to the manufacturer's guidelines.

Thioglycollate-Induced Peritonitis—

Male C57B1/6 mice 5-6 weeks old were injected intraperitoneally with 1 ml sterile 4% (wt/vol) thioglycollate (Sigma-Aldrich). Mice were injected with 16.5 mg/kg 6-B345TTQ, 6-234TTQ or the equal volume of vehicle only every 8-12 hours. At various time points after injection, mice were sacrificed and subjected to peritoneal lavage with 4 ml PBS containing 5 mM EDTA and 1% BSA. Total leukocytes in lavage samples were enumerated with a hemocytometer. Cells ($1\times10^5$) were attached to glass slides with a Cytospin4 instrument (ThermoSharidon) and stained with modified Wright-Giemsa stain. Differential cell counts were performed on 5 individual fields, each containing 100 cells by light microscopy.

Example 1

High-Throughput Screening

To identify small molecule inhibitors for the leupaxin/paxillin α4-integrin interaction an ELISA assay was used (FIG. 1A) at the ICCB Longwood screening facilities at Harvard Medical School, Boston, Mass. 6×His-recombinant integrin cytoplasmic tail model proteins (α4 and αIIb) were cloned (34; 35) and modified by inserting a sequence encoding the peptide, GLNDIFEAQKIEWHE, at the NdeI site immediately downstream of the thrombin cleavage site. This peptide incorporates biotin in vivo upon expression in *Escherichia coli* by biotin ligase. Proteins were expressed and purified from *E. coli* extracts (35) (FIG. 1B). A total of 40,000 compounds was screened at a concentration of 16 μg/ml using the Mixed Commercials 1, 2 & 4, ChemDiv 1 & 2, Specplus, Maybridge 2 & 3, Peakdale2, Starr Foundation Extracts 1 & 2, Philippines Plant Extracts 2, DDS 2, Biomol ICCB known bioreactives, Bionet 2, Enamine 1, IF Lab 1 libraries (http://iccb.med.harvard.edu/screening/compound_libraries/index.htm). As a positive control for inhibition we used compound A7B7C7 (13) at a final concentration of 25 μM. Compounds that showed inhibition of at least 60% were considered screening positives. A total of 194 compounds (approximately 0.5% of the compounds screened) met this criterion. 0.3% (=115 compounds) were then retested in the ELISA assay at different concentrations. 25 (0.06%) of the total compounds screened were confirmed as screening positives (FIG. 1C).

Example 2

Figure 2:
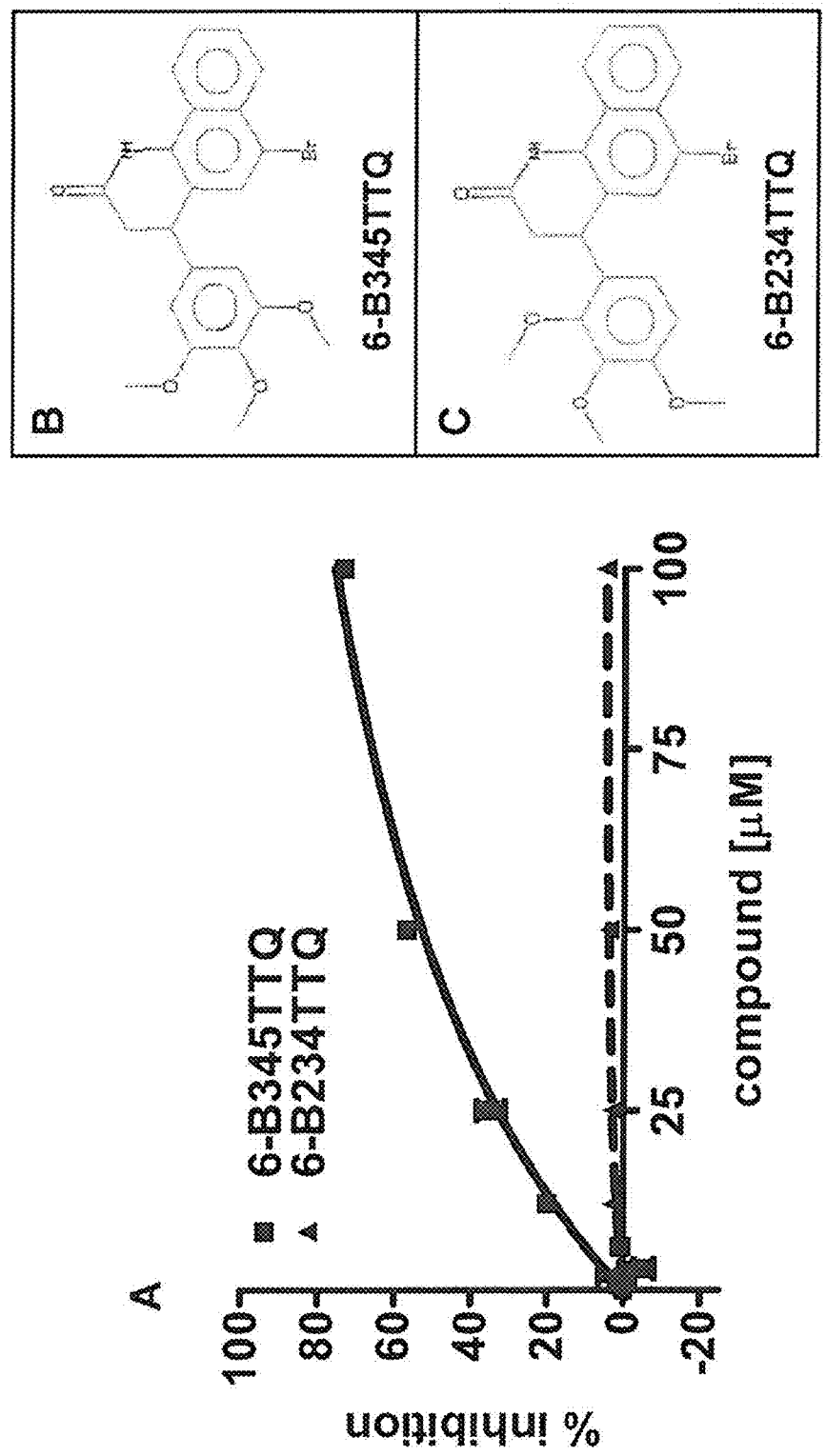
FIG. 2A depicts a graph charting the results after a biotinylated α4 tail was immobilized to neutraviding coated ELISA plates and incubated with 10 μg/ml leupaxin in the presence of increasing concentrations of 6-B345TTQ or 6-B234TTQ.
FIG. 2B depicts the structure of the active-compound 6-B345TTQ.
FIG. 2C depicts the structure of the inactive compound 6-B234TTQ.
Figure 3:
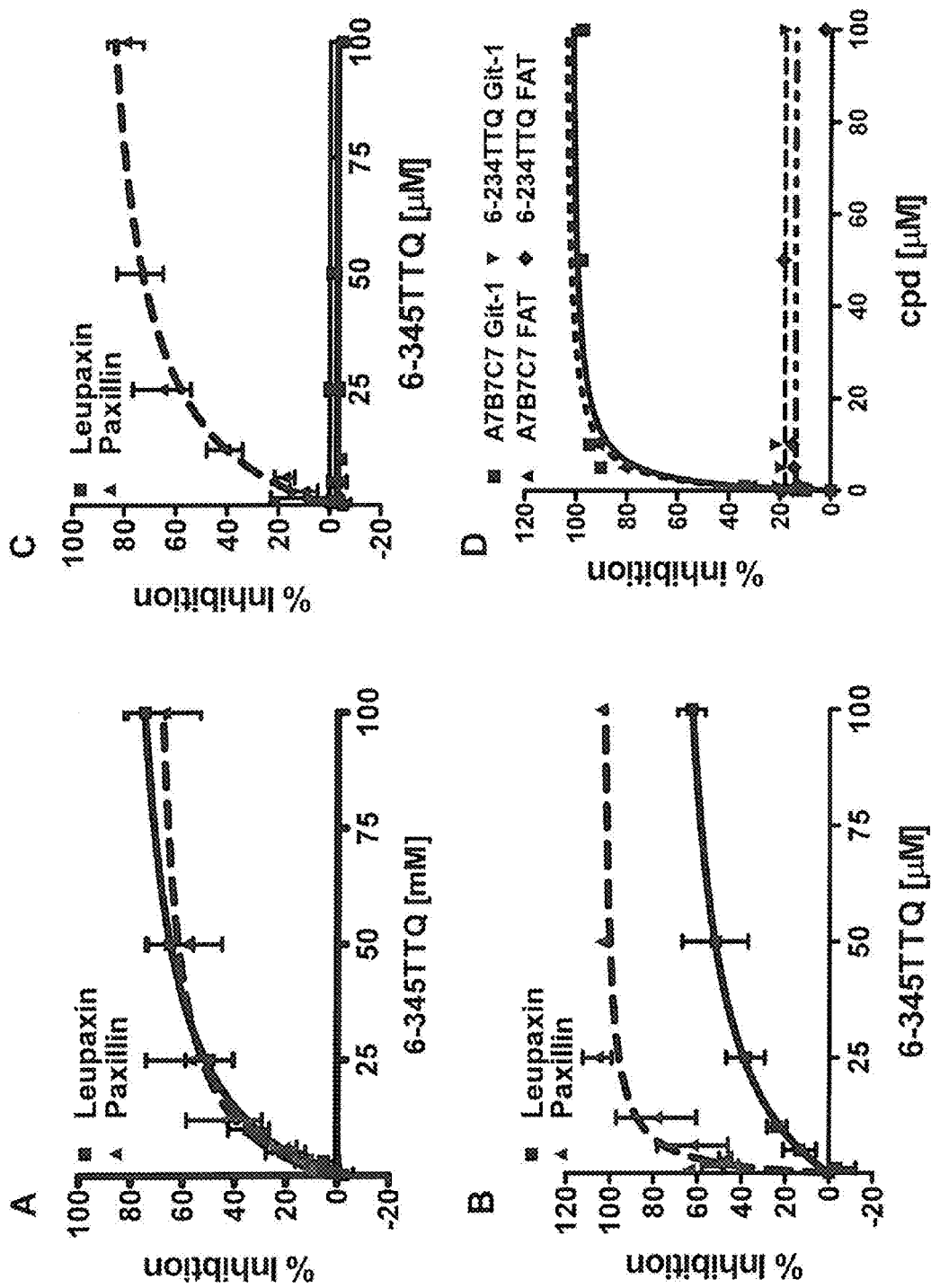
FIG. 3 depicts graphs plotted from ELISA results for: A, Inhibition of binding to α4. Biotinylated α4 tail protein was immobilized to neutraviding coated ELISA plates and incubated with 10 μg/ml leupaxin or paxillin in the presence of increasing concentrations of compound 6-B345TTQ. B, Inhibition of binding to Git-1. Recombinant Git-1 was immobilized on ELISA plates and incubated with 10 μg/ml leupaxin or paxillin in the presence of increasing concentrations of compound 6-B345TTQ. C, Inhibition of binding to FAT. Recombinant FAT was immobilized on ELISA plates and incubated with 10 μg/ml leupaxin or paxillin in the presence of increasing concentrations of compound 6-B345TTQ. D, the inactive isomer 6-234TTQ did not inhibit the interaction of paxillin with either FAT or Git-1. A7B7C7 inhibited the interaction of paxillin with both FAT and Git-1.

Compound 6-B345TTQ Inhibits the Interaction of α4-Integrin with Leupaxin Acting as a Competitive Inhibitor In dose response ELISA binding assays the inhibitory effect of compound 6-B345TTQ (ChemDiv, San Diego, Calif.) was verified for the interaction of leupaxin with α4-integrin. Interestingly, an isomer (6-B234TTQ (ChemDiv, San Diego, Calif.)) that differed in the position of one methoxy group was completely inactive towards the leupaxin α4 interaction (FIG. 2) establishing the exquisite structural specificity of this effect. The effect of compound 6-B345TTQ on other protein-protein interactions that are involved in α4-mediated cell migration to assess its specificity in inhibiting the α4-leupaxin interaction was determined. Compared to A7B7C7 which inhibited the interaction of leupaxin with the focal adhesion targeting sequence of pp125$^{FAK}$ with an IC$_{50}$ of 300 nM, 6-B345TTQ had no effect on the binding of FAT to leupaxin at concentrations up to 100 μM (FIG. 3C). Interestingly, it did inhibit the interaction of FAT with paxillin. Comparing the effect of 6-B345TTQ on the interaction of α4-integrin with different paxillin paralogues, it was found that leupaxin and paxillin binding were inhibited with IC$_{50}$ of 18 μM and 10.8 μM, respectively (FIG. 3A). To further investigate the characteristics of the inhibitor its effect on the interaction of leupaxin or paxillin with the Arf-GAP Git-1, which binds to the LD4-motif of paxillin, was determined (37, 38). Compound 6-B345TTQ had a strong inhibitory effect on the interaction of GIT-1 with paxillin (IC$_{50}$=2.4 μM) and a weaker effect on its interaction with leupaxin (IC$_{50}$=25 μM) (FIG. 3B). In contrast, the inactive isomer 6-234TTQ did not inhibit the interaction of paxillin with either FAT or Git-1 (FIG. 3D). The previously identified peptide A7B7C7, inhibited the interaction of paxillin with both, FAT and Git-1 (IC$_{50}$=1.8 or 1.7 μM, respectively) (FIG. 3D).

Figure 4:
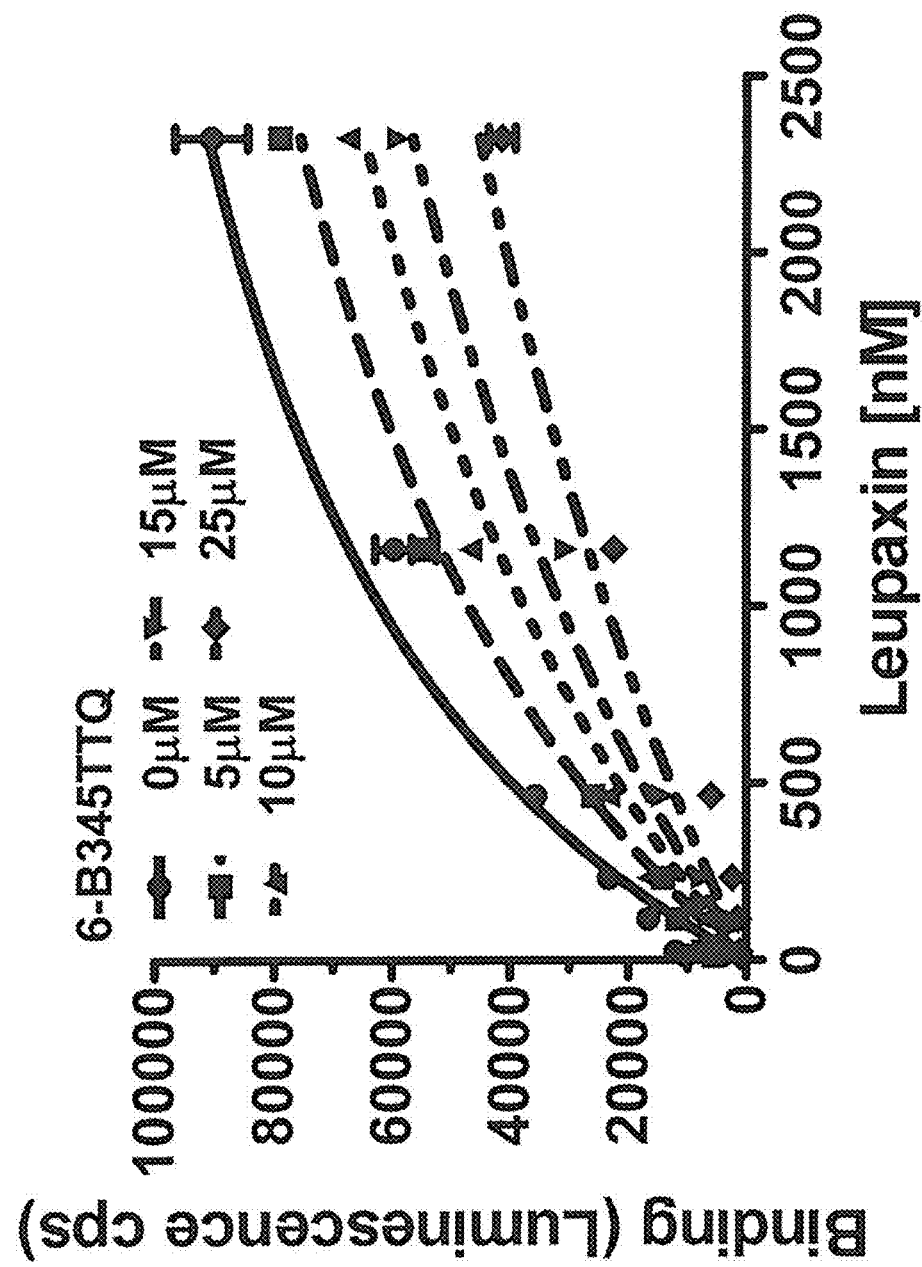
FIG. 4 depicts a graph of the results from an ELISA using biotinylated recombinant α4-tails immobilized on neutravidin coated 96-well plates. Bound proteins were incubated with increasing concentrations of HA-tagged recombinant leupaxin in the presence or absence of compound 6-345TTQ. Bound leupaxin was detected by incubation with an anti HA-tag antibody followed by HRP-conjugate and detected by luminescence. Data were fitted to equations for models of competitive, non-competitive, uncompetitive or mixed inhibition.

To investigate the nature of inhibition by 6-345TTQ, the α4 tail, model protein was immobilized to ELISA plates and incubated with increasing concentrations of leupaxin in the presence or absence of various concentrations of the inhibitor. Inhibition was overcome by increasing concentrations of leupaxin indicating that 6-345TTQ acts as a competitive inhibitor. To confirm this hypothesis, data were fitted to equations of different models for inhibition using Graph Pad Prism 5.0 (FIG. 4). The model for competitive inhibition fit the data best with $r^2=0.9690$. Furthermore, we used the mixed model to fit the data resulting in α-values of ~$2.958\times10^{12}$. When α is very large, binding of the inhibitor prevents binding of the substrate and the mixed-model becomes identical to competitive inhibition. These results indicate that 6-345TTQ acts as a competitive inhibitor.

Figure 5:
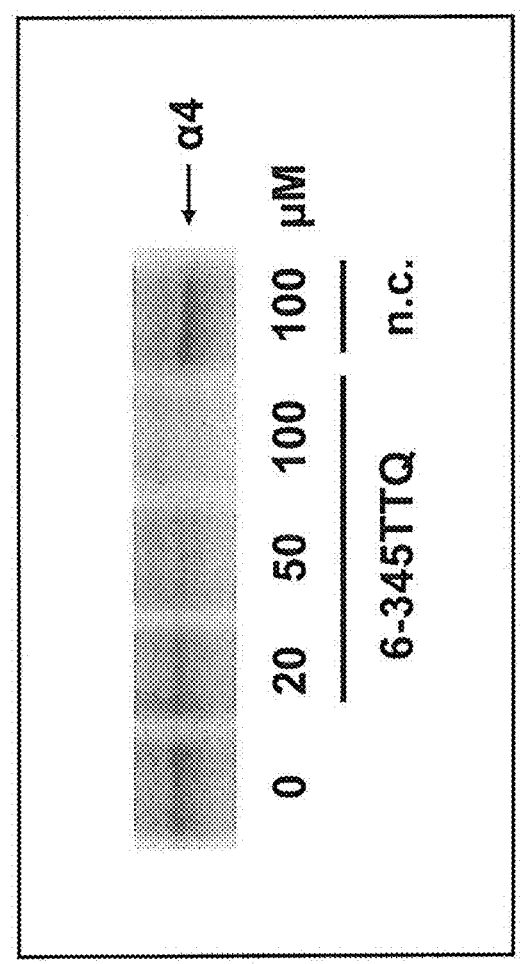
FIG. 5 depicts an anti-biotin immunoblot after paxillin was immunoprecipitated from surface biotin-labeled Jurkat T Cells in the presence of increasing concentration of compound 6-345TTQ or the control compound (n.c.). Co-immunoprecipitated α4 integrin was visualized by blotting for biotin after separation in SDS-PAGE.

To directly confirm the effect of compound 6-345TTQ on the interaction of native paxillin and α4-integrin, paxillin was immunoprecipitated from Jurkat T cells in the absence or presence of the compound (FIG. 5). In paxillin immunoprecipitates, α4-integrin was present and the amount of co-immunoprecipitated α4 decreased with increasing concentrations of 6-345TTQ. The control compound 6-234TTQ did not reduce the amount of precipitated α4.

Example 3

Figure 6:
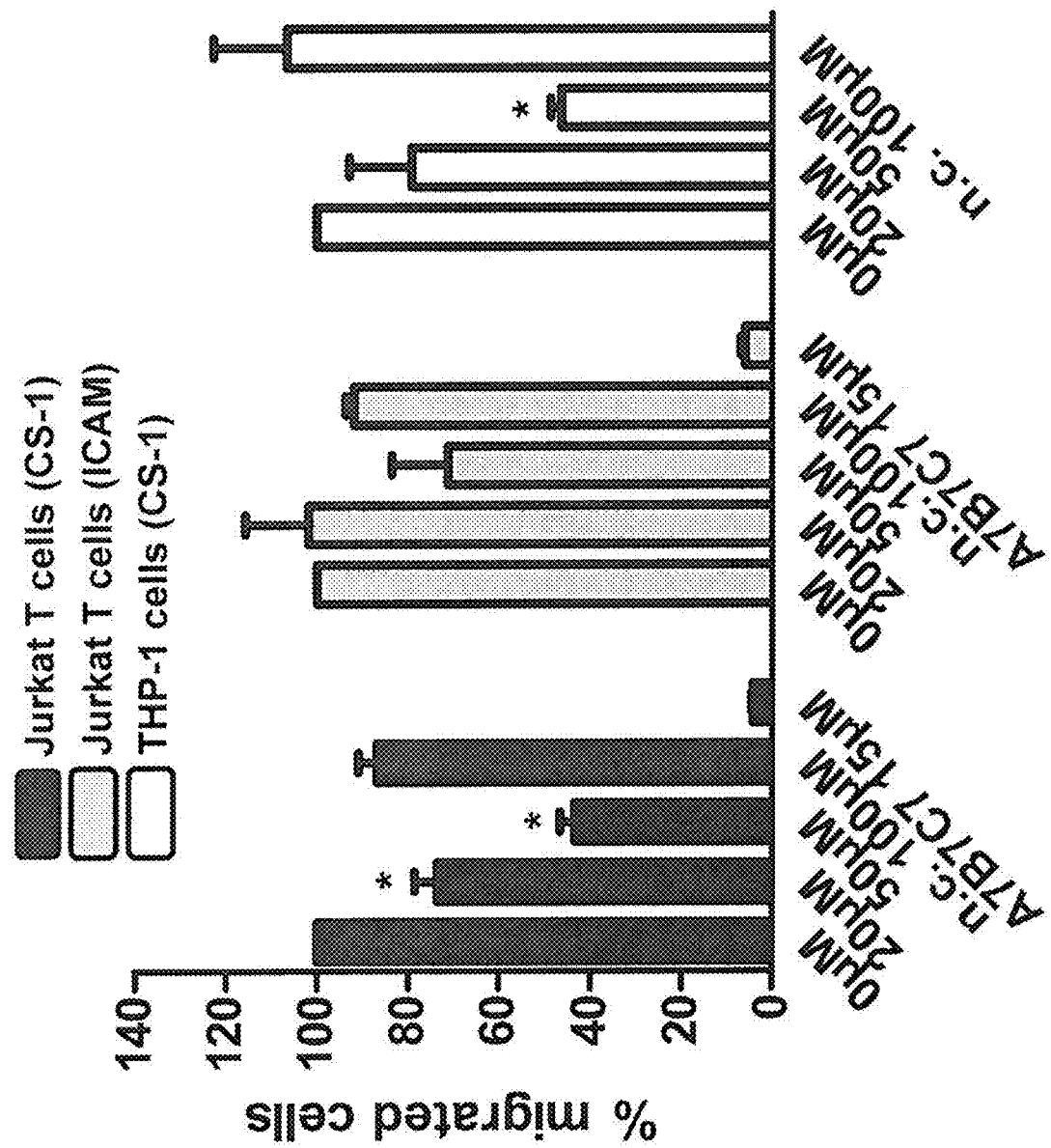
FIG. 6 is a graph showing the effect of 6-345TTQ on cell migration. Cell migration was assayed in a modified Boyden chamber assay. Transwell (Costar) polycarbonate membranes were coated with 10 μg/ml CS-1 or 20 μg/ml ICAM. $1.0 \times 10^5$ THP-1 cells or $2.0 \times 10^5$ Jurkat cells were added to the top chamber and allowed to migrate for 3 and 5 hours, respectively. Cells in the bottom chamber were enumerated using a hemacytometer. Small molecule inhibitors were added to the top and bottom chamber at indicated concentrations, (n.c.=negative control compound).
Figure 8:
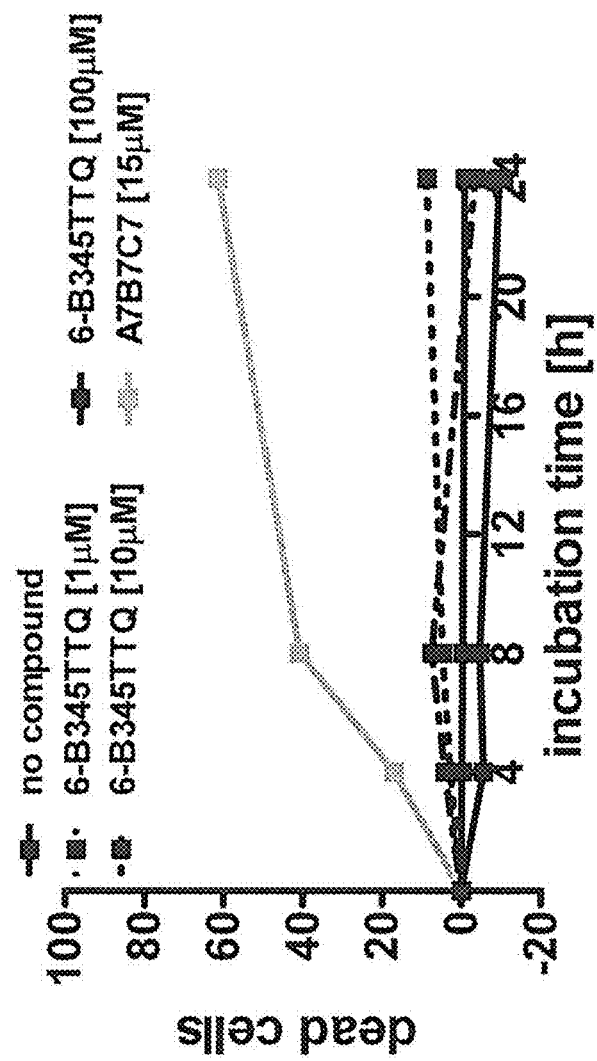
FIG. 8 is a graph depicting cell migration in JB4-Y991A T cells. Cell migration was assayed in a modified Boyden chamber assay. Transwell (Costar) polycarbonate membranes containing 0.3-μm pores were coated with 10 μg/ml CS-1 or 20 μg/ml ICAM. $2.0 \times 10^5$ JB4-Y991A or Jurkat cells in RPMI 1640 with 10% fetal bovine serum were added to the top chamber and allowed to migrate for 5 hours at 37° C. towards SDF-1α. Cells in the bottom chamber were enumerated with a hemacytometer. Small molecule inhibitors were added to the top and bottom chamber in the indicated concentrations.

Compound 6-B345TTQ Inhibits α4-Mediated Migration of T-Cell and Monocyte Cell Lines and Enhances Cell Spreading The ability of α4 to enhance cell migration is dependent on the binding of paxillin (11, 34) leading to an investigation of the effect of compound 6-B345TTQ on Jurkat T cell or THP-1 monocyte migration. Directed α4-mediated migration was assessed in a modified Boyden chamber using fibronectin CS-1 fragment (α4 integrin-specific ligand) as a substrate. Cells were tested in the absence or presence of different concentrations of 6-B345TTQ. The compound inhibited monocyte and T-cell migration in a dose dependent manner with 52.6% and 56.4% inhibition of migration at 50 μM, respectively (FIG. 6B). In contrast, residual α4-dependent migration of Jurkat T cells expressing a mutated α4-integrin (α4(Y991A)) which exhibits reduced paxillin binding (8) was not further decreased by incubation with 6-B345TTQ (FIG. 8), indicating that the compound specifically inhibits α4-mediated cell migration by blocking paxillin binding.

Figure 7:
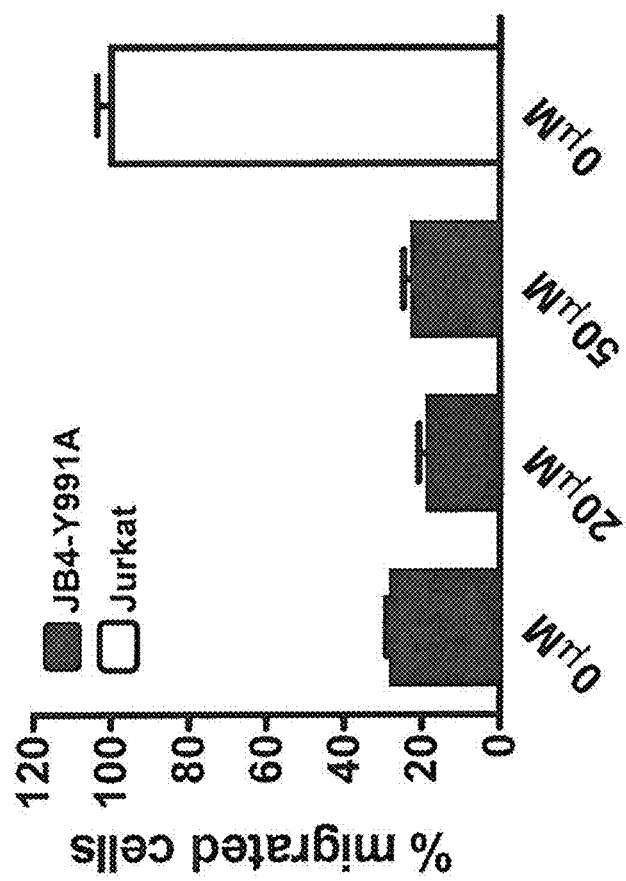
FIG. 7 is a graph depicting the cytotoxic effect of compounds on cultivated Jurkat T cells. The effects were determined using the CellTiter 96® Aqueous One Solution Cell Proliferation Assay (Promega, Madison, Wis.) according to the manufacturer's guidelines. Results are mean±SEM of 5 independent experiments. *$P<0.05$ compared to no added compound, 2-tailed student's t-test.

To further evaluate the specificity of compound 6-B345TTQ, its impact on αLβ2-mediated Jurkat T cell migration on ICAM-1 was assayed. Cell migration on ICAM-1 was not significantly reduced (FIG. 6B). The 6-B234TTQ isomer (n.c.) that did not inhibit the α4-paxillin or -leupaxin interactions had no effect on Jurkat cell migration on CS-1 or ICAM-1. In contrast, compound A7B7C7 decreased Jurkat cell migration on both substrates, emphasizing its lack of specificity relative to 6-B345TTQ (FIG. 6B). The lack of effect on αLβ2-mediated migration indicates that compound 6-B345TTQ specifically inhibits α4-mediated Jurkat T cell migration and does not impair the general migration machinery. As an additional test for toxicity of this compound, we examined its effects on cell viability; the compound was not cytotoxic at concentrations up to 100 μM for 24 h. In sharp contrast, incubation with 50 μM A7B7C7 for 24 h led to 62% dead cells after 24 h of incubation (FIG. 7).

Figure 9:
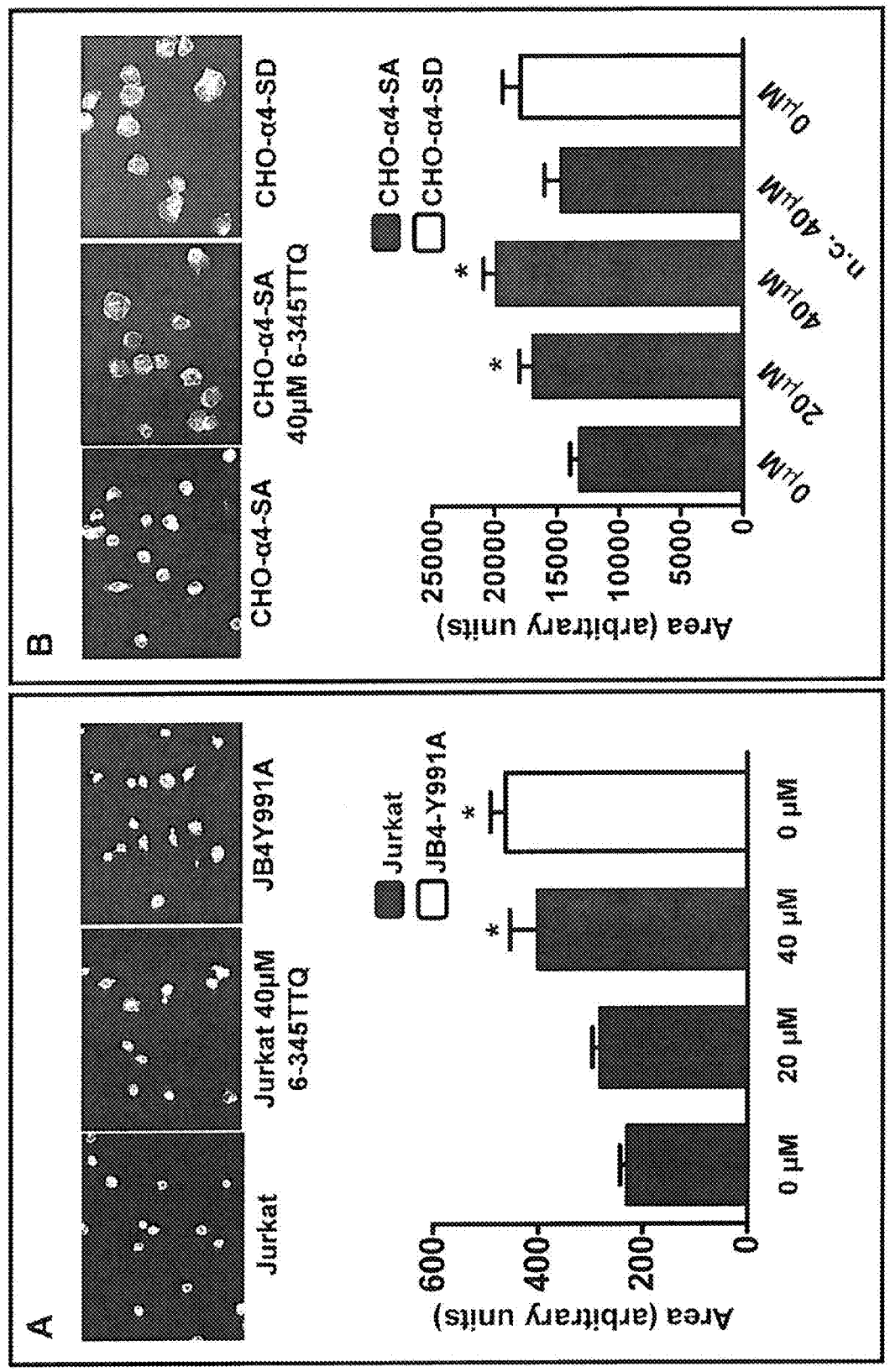
FIG. 9 depicts either Jurkat cells, JB4-Y991A (A) cells or CHO cells (B) after resuspension in Dulbecco's modified Eagle's medium or RPMI 1640, respectively, containing 0.5% fetal bovine serum and 0.2% BSA. Cells were plated on coverslips coated with 3 μg/ml GST-CS-1 in 12 well plates in the presence or absence of small molecule inhibitors. After spreading for 45 or 180 minutes at 37° C., respectively, cells were fixed, permeabilized and stained with rhodamine-conjugated phalloidin. The cell area was measured and analyzed using the NIH Image J software. Results are shown as mean±SEM. At least three independent experiments were performed and in each experiment at least 30 cells were analyzed. *$P<0.05$, compared to no added compound, 2-tailed student's t-test. (n.c.=negative control compound)

Expression of a phosphorylation-mimicking α4 variant in CHO cells (CHO-α4S998D cells) leads to reduced cell migration and enhanced cell spreading due to the disruption of paxillin binding to α4 (31). In Contrast, CHO cells that express the non-phosphorylatable mutant (CHO-α4S998A cells) have a spreading defect (30, 31) due to increased paxillin binding and the resulting recruitment of Arf-GAPs such as Git-1 (39). Therefore, the spreading defect of CHO-S998A cells was used as a convenient readout for biological consequences of inhibition of paxillin binding to α4-integrin by 6-B345TTQ. CHO-S998A cells were plated on CS-1 coated cover slips and were allowed to spread for 45 minutes in the presence of increasing concentrations of 6-B345TTQ. Incubation with the compound increased the spreading of CHO-S998A cells to a level comparable with CHO-S998D cells whereas the control compound 6-234TTQ had no effect (FIG. 9B). The same results were observed in Jurkat T cells when spreading was assessed 180 minutes after plating on CS-1 using JB4-Y991A cells as control. In presence of increasing concentrations of the compound a dose dependent increase of cell spreading was observed reaching a level comparable to that of JB4-Y991A cells (FIG. 9A). In contrast, when CHO wildtype cells that do not express α4 were plated on fibronectin and treated with compound 6-B345TTQ cell spreading was not increased (data not shown).

Example 4

Figure 10:
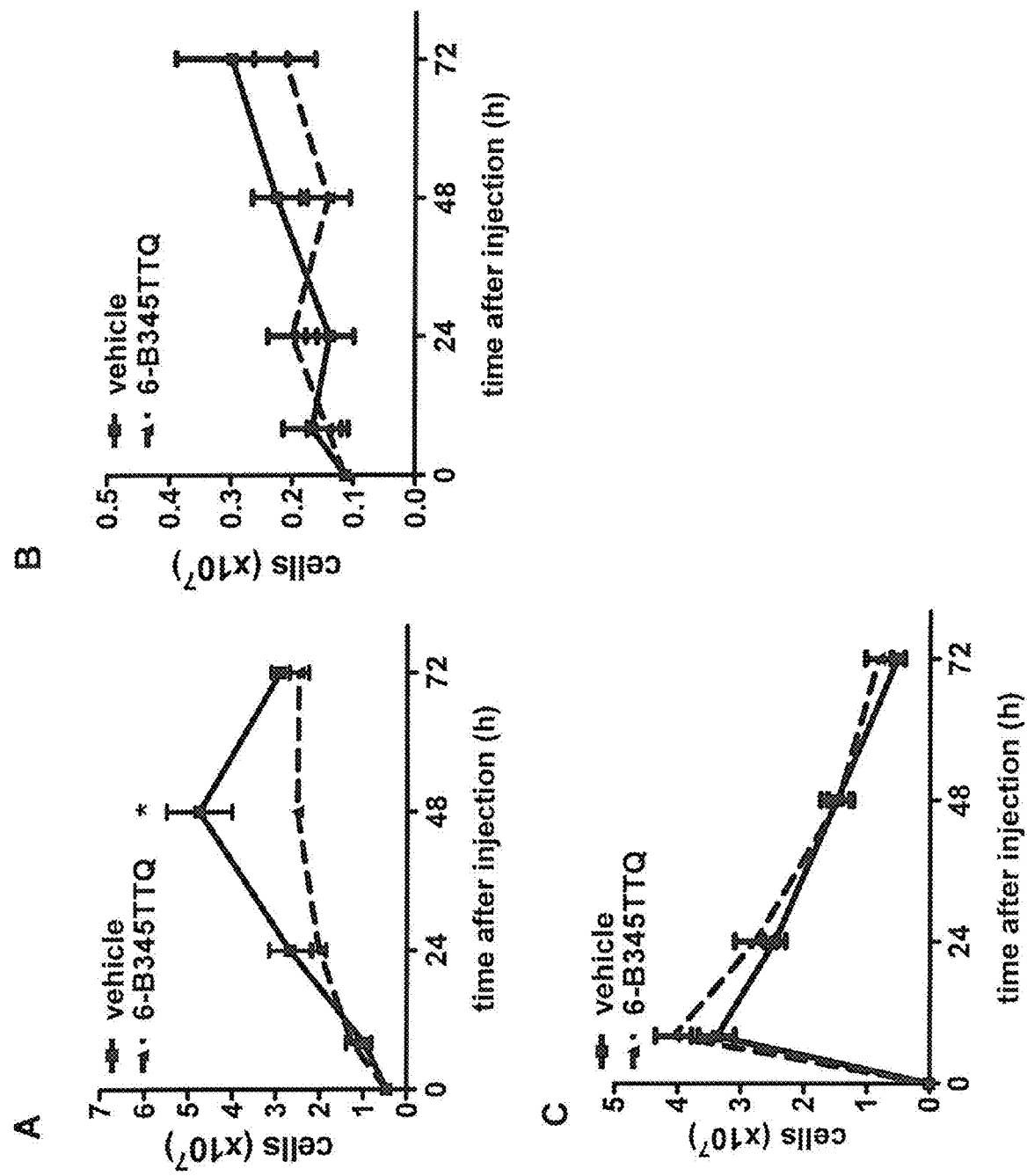
FIG. 10 depicts graphs demonstrating the recruitment of mononuclear leukocytes to the peritoneum in response to thioglycollate. C57B1/6 mice were injected intraperitoneally with 1 ml sterile 4% (wt/vol) thioglycollate (Sigma-Aldrich). Mice were treated with 16.5 mg/kg 6-B345TTQ or the equal volume of vehicle every 8-12 hours by i.p. injection. At various time points after injection, mice were sacrificed and subjected to peritoneal lavage with 4 ml PBS containing 5 mM EDTA and 1% BSA. Total leukocytes in the lavage samples were enumerated with a hemocytometer and differential cell counts were performed on cytospin slides after modified Wrigh-Giemsa staining. Results are shown for total monocyte/macrophages (A), lymphocyte (B) and neutrophil (C) counts. *$P<0.05$, 2-tailed student's t-test. Results are mean±SEM of 10 mice of 3 separate experiments.

6-B345TTQ Impairs the Recruitment of Mononuclear Leukocytes to an Inflammatory Site To directly test the effect of compound 6-B345TTQ on leukocyte recruitment in vivo, C57B1/6 mice were intraperitoneally injected with thioglycollate to induce inflammation. Mice Were injected with 16.5 mg/kg 6-B345TTQ or 6-234TTQ (control compound) or the equal volume of vehicle every 8-12 hours. Mice that were injected with vehicle showed a 10.5-fold increase in peritoneal monocytes/macrophages 48 hours after thioglycollate injection. In mice that were treated with 6-B345TTQ infiltration of monocytes/macrophages was reduced by 50% (FIG. 10A). The recruitment of lymphocytes to the peritoneum was also reduced 48 hours and 72 hours after thioglycollate injection in mice that were injected with 6-B345TTQ compared to control mice, but this reduction was not statistically significant. There was no difference in the recruitment of neutrophils in response to thioglycollate between mice that were injected with the compound or with vehicle only. Furthermore, the control compound 6-234TTQ had no effect on leukocyte migration into the inflamed peritoneum (data not shown).

Example 5

Lymphangiogenesis Depends on Integrin α4β1 Signal Transduction

Figure 11:
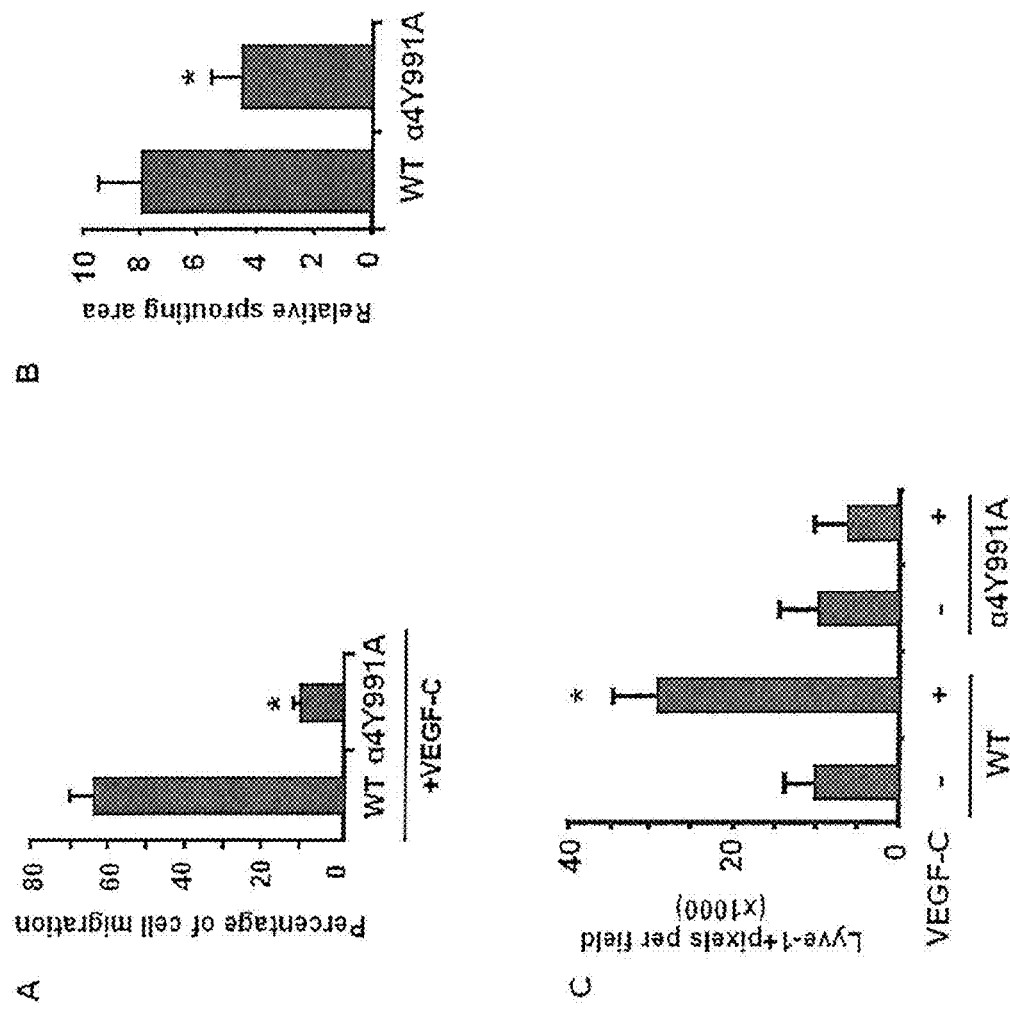
FIGS. 11A-11C depict results demonstrating integrin α4Y991A mutation suppresses LEC invasion and lymphangiogenesis.

To explore the importance of integrin α4β1 signaling in LECs, we isolated LECs from mice with an integrin α4Y991A knock-in mutation (29). This mutation in the cytoplasmic tail of integrin α4β1 disrupts integrin α4β1-mediated association with paxillin and talin (12, 41, 42) and blocks α4β1-mediated leukocyte adhesion (42). Although LECs isolated from WT and integrin α4Y991A mice expressed similar levels of integrin α4β1 (40), LECs from α4Y991A mice did not polarize or develop mature paxillin-containing focal adhesions when adhering to CS-1 fibronectin (FIG. 11A, left). Importantly, α4Y991A LECs failed to migrate in response to VEGF-C (FIG. 11A, right). Additionally, VEGF-C stimulated ex vivo lymphatic vessel sprouting from isolated thoracic ducts (large lymphatic vessels) when isolated from WT but not α4Y991A animals (FIG. 11B). Finally, VEGF-C stimulated lymphangiogenesis in Matrigel plugs in vivo was completely inhibited in integrin α4Y991A mice (FIG. 11C). In fact, integrin α4β1 association with paxillin was suppressed in VEGF-C containing Matrigel plugs from α4Y991A mice, and few α4+ paxillin+ vessels with well-formed lumen were observed in mutant mice (40). These results indicate that integrin α4β1 expression and signal transduction are required for LEC migration and invasive responses to lymphangiogenesis factors in vitro and during in vivo lymphangiogenesis.

EQUIVALENTS

While this invention has been particularly shown and described with references to preferred embodiments thereof, it will be understood by those skilled in the art that various changes in form and details may be made therein without departing from the scope of the invention encompassed by the appended claims.

The inventions illustratively described herein can suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the future shown and described or any portion, thereof, and it is recognized that various modifications are possible within the scope of the invention claimed. Thus, it should be understood that although the present invention has been specifically disclosed by preferred embodiments and optional features, modification and variation of the inventions herein disclosed can be resorted by those skilled in the art, and that such modifications and variations are considered to be within the scope of the inventions disclosed herein. The inventions have been described broadly and generically herein. Each of the narrower species and subgeneric groupings falling within the scope of the generic disclosure also form part of these inventions. This includes the generic description of each invention with a proviso or negative limitation removing any subject matter from the genus, regardless of whether or not the excised materials specifically resided therein.

In addition, where features or aspects of an invention are described in terms of the Markush group, those schooled in the art will recognize that the invention is also, thereby described in terms of any individual member or subgroup of members of the Markush group. It is also to be understood that the above description is intended to be illustrative and not restrictive. Many embodiments will be apparent to those of in the art upon reviewing the above description. The scope of the invention should therefore, be determined not with reference to the above description, but should instead be determined with reference to the appended claims, along with the full scope of equivalents to which such claims are entitled. The disclosures of all articles and references, including patent publications, are incorporated herein by reference.

REFERENCES

The following references are cited in the specification by reference number; all of these references are incorporated by this reference in the application in their entirety:

1. Ransohoff, R. M., Kivisakk, P., and Kidd, G. 2003. Three or more routes for leukocyte migration into the central nervous system. *Nat. Rev. Immunol* 3:569-581.
2. Smolen, J. S. and Steiner, G. 2003. Therapeutic strategies for rheumatoid arthritis. *Nat. Rev. Drug Discov.* 2:473-488.
3. James, W. G., Bullard, D. C., and Hickey, M. J. 2003. Critical Role of the alpha(4) Integrin/VCAM-1 Pathway in Cerebral Leukocyte Trafficking in Lupus-Prone MRL/fas (lpr) Mice. *J Immunol.* 170:520-527.
4. von Andrian, U. H. and Engelhardt, B. 2003. Alpha4 integrins as therapeutic targets in autoimmune disease, *N. Engl. J Med.* 348:68-72.
5. Miller. D. H., Khan, O. A., Sheremata, W. A., Blumhardt, L. D., Rice, G. P., Libonati, M. A., Willmer-Hulme, A. J., Dalton, C. M., Miszkiel, K. A., and O'Connor, P. W. 2003. A controlled trial of natalizumab for relapsing multiple sclerosis. *N. Engl. J Med.* 348:15-23.
6. Arroyo, A. G., Yang, J. T., Rayburn, H., and Hynes, R. O. 1996. Differential requirements for α4 integrins in hematopoiesis. *Cell* 85:997-1008.
7. Sheridan, C. 2005. Third Tysabri adverse case hits drug class. *Nat Rev. Drug Discov.* 4:357-358.
8. Rose. D. M., Liu, S., Woodside, D. G., Han, J., Schlaepfer, D. D., and Ginsberg, M. H. 2003. Paxillin Binding to the {alpha}4 integrin subunit stimulates LFA-1 (Integrin {alpha}L{beta}2)-dependent T Cell migration by augmenting the activation of focal adhesion kinase/proline-rich tyrosine kinase-2. *J Immunol* 170:5912-5918.
9. Ylanne, J., Chen, Y. -P., O'Toole, T. E., Loftus, J. C., Takada, Y., and Ginsberg, M. H. 1993. Distinct functions of integrin a and b subunit cytoplasmic domains in cell spreading and formation of focal adhesions. *J. Cell Biol.* 122:223-233.
10. Rose, D. M., Grabovsky, V., Alon, R., and Ginsberg, M. H. 2001. The Affinity of Integrin alpha(4)beta(1) Governs Lymphocyte Migration. *J. Immunol.* 167:2824-2830.
11. Liu, S., Thomas, S. M., Woodside, D. G., Rose, D. M., Kiosses, W. B., Pfaff, M., and Ginsberg, M. H. 1999. Paxillin binding to alpha 4 integrins modifies integrin-dependent biological responses. *Nature* 402:676-681.
12. Liu, S., Kiosses, W., Rose, D. M., Slepak, M., Salgia, R., Griffin, J. D., Turner, C. E., Schwartz, M. A., and Ginsberg, M. H. 2002. A fragment of Paxillin binds the alpha 4 integrin cytoplasmic domain (Tail) and selectively inhibits alpha 4-mediated cell migration. *J. Biol. Chem.* 277: 20887-20894.
13. Ambroise, Y., Yaspari, B., Ginsberg, M. H., and Boger, D. L. 2002. Inhibitors of cell migration that inhibit intracellular paxillin/alpha4 binding. A well-documented use of positional scanning libraries. *Chem. Biol.* 9:1219-1226.
14. Yang, J. T., Rayburn, H., and Hynes, R. O. 1995, Cell adhesion events mediated by alpha 4 integrins are essential in placental and cardiac development. *Development* 121: 549-560.
15. Scott, L. M., Priestley, G. V., and Papayannopoulou, T. 2003. Deletion of alpha4 integrins from adult hematopoietic cells reveals roles in homeostasis, regeneration, and homing. *Mol. Cell Biol* 23:9350-9361.
16. Arroyo, A. G., Yang, J. T., Rayburn, H., and Hynes, R. O. 1999. Alpha4 integrins regulate the proliferation/differentiation balance of multilineage hematopoietic progenitors in vivo. *Immunity.* 1:555-566.
17. Papayannopoulou, T. and Craddock, C. 1997. Homing and trafficking of hemopoietic progenitor cells. *Acta Haematol.* 97:97-104.
18. Oostendorp, R. A., Ghaffari, S., and Eaves, C. J. 2000. Kinetics of in vivo homing and recruitment into cycle of hematopoietic cells are organ-specific but CD44-independent. *Bone Marrow Transplant.* 26:559-566.
19. Lo, C. G., Lu, T. T. and Cyster, J. G, 2003, Integrin-dependence of lymphocyte entry into the splenic white pulp. *J Exp Med.* 197:353-361.
20. Lu, T. T. and Cyster, J. G. 2002. Integrin-mediated long-term B cell retention in the splenic marginal zone. *Science* 297:409-412.
21. Sengbusch, J. K., He, W., Pinco, K. A., and Yang, J. T. 2002. Dual functions of [alpha]4[beta]1 integrin in epicardial development: initial migration and long-term attachment. *J Cell Biol* 157:873-882.
22. Young, B. A., Taooka, Y., Liu, S., Askins, K. J., Yokosaki, Y., Thomas, S. M., and Sheppard, D. 2001, The cytoplasmic domain of the integrin alpha9 subunit requires the adaptor protein paxillin to inhibit cell spreading but promotes cell migration in a paxillin-independent manner. *Mol. Biol Cell* 12:3214-3225.
23. Finke, D., Acha-Orbea, H., Mattis, A., Lipp, M., and Kraehenbuhl, J. 2002. CD4+CD3− cells induce Peyer's patch development: role of alpha4beta1 integrin activation by CXCR5. *Immunity,* 17:363-373.

24. Finke, D. and Kraehenbuhl, J. P. 2001. Formation of Peyer's patches. *Curr. Opin. Genet. Dev.* 11:561-567.
25. Hyduk, S. J., Oh, J., Xiao, H., Chen, M., and Cybulsky, M. I. 2004. Paxillin selectively associates with constitutive and chemoattractant-induced high-affinity alpha4beta1 integrins: implications for integrin signaling. *Blood* 104: 2818-2824.
26. Quinn, M. J., Plow, E. F., and Topol, E. J. 2002. Platelet glycoprotein IIb/IIIa inhibitors: recognition of a two-edged sword? *Circulation,* 106:379-385.
27. Kaushansky, K., Broudy, V. C., Grossmann, A., Humes, J., Lin, N., Ren, H. P., Bailey, M. C, Papayannoppulou, T., Forstrom, J. W., and Sprugel, K. H. 1995. Thrombopoietin expands erythroid progenitors, increases red cell production, and enhances erythroid recovery after myelosuppressive therapy. *J Clin. Invest* 96:1683-1687.
28. Goodyear, C. S. and Silverman, G. J. 2003. Death by a B cell superantigen: In vivo VH-targeted apoptotic supraclonal B cell deletion by a Staphylococcal Toxin. *J Exp Med.* 197:1125-1139.
29. Feral, C. C., Rose, D. M., Han, J., Fox, N., Silverman, G. J., Kaushansky, K., and Ginsberg, M. H. 2006, Blocking the α4 integrin-paxillin interaction selectively impairs mononuclear leukocyte recruitment to an inflammatory site. *J Clin. Invest* 116: 715-723.
30. Goldfinger, L. E., Han, J., Kiosses, W. B., Howe, A. K., and Ginsberg, M. H. 2003. Spatial restriction of α4 integrin phosphorylation regulates lamellipodial stability and α4β1-dependent cell migration. *J Cell Biol.* 162: 731-741.
31. Han, J., Rose, D. M., Woodside, D. G., Goldfinger, L. E., and Ginsberg, M. H. 2003. Integrin $\alpha_4\beta_1$-dependent T Cell Migration Requires Both Phosphorylation and Dephosphorylation of the $\alpha_4$ Cytoplasmic Domain to Regulate the Reversible Binding of Paxillin. *J Biol. Chem.* 278: 34845-34853.
32. Ramos, J. W., Hughes, P. E., Renshaw, M. W., Schwartz, M. A., Formstecher, E., Chneiweiss, H., and Ginsberg, M. H. 2000. Death Effector Domain Protein PEA-15 Potentiates Ras Activation of Extracellular Signal Receptor-activated Kinase by an Adhesion-independent Mechanism. *Mol. Biol. Cell* 11: 2863-2872.
33. Jongewaard, I. N., Tsai, P. M., and Smith, J. W. 1996. The type III connecting segment of fibronectin contains an aspartic acid residue that regulates the rate of binding to integrin alpha 4 beta 1, *Cell Adhes. Commun.* 3: 487-495.
34. Liu, S. and Ginsberg, M. H. 2000. Paxillin binding to a conserved sequence motif in the alpha 4 integrin cytoplasmic domain. *J Biol Chem.* 275: 22736-42.
35. Pfaff, M., Liu, S., Erle, D. J., and Ginsberg, M. H. 1998. Integrin beta cytoplasmic domains differentially bind to cytoskeletal proteins. *J Biol Chem.* 273: 6104-9.
36. Schatz, P. J. 1993. Use of peptide libraries to map the substrate specificity of a peptide-modifying enzyme: a 13 residue consensus peptide specifies biotinylation in *Escherichia coli. Biotechnology* (N.Y.) 11: 1138-1143.
37. Turner, C. E., Brown, M. C., Perrotta, J. A., Riedy, M, C, Nikolopoulos, S. N., McDonald, A. R., Bagrodia, S., Thomas, S., and Leventhal, P. S. 1999. Paxillin LD4 motif binds PAK and PIX through a novel 95-kD ankyrin repeat, ARF-GAP protein: A role in cytoskeletal remodeling. *J Cell Biol.* 145: 851-63.
38. Zhao, Z. S., Manser, E., Loo, T. H., and Lim, L. 2000. Coupling of PAK-interacting exchange factor PIX to GIT1 promotes focal complex disassembly. *Mol Cell Biol* 20: 6354-63.
39. Nishiya, N., Kiosses, W. B., Han, J., and Ginsberg, M. H. 2005. An [alpha]4 integrin-paxillin-Arf-GAP complex restricts Rac activation to the leading edge of migrating cells *Nat. Cell Biol:* 7: 343-352.
40. Garmy-Susini, B., Avraamides, C. J., Schmid, M. C., Fbubert, P., Ellies, L. G., Barnes, L., Feral, C., Papayannopoulou, T., Lowy, A., Blair, S. L., Cheresh, D., Ginsberg, M., Varner, J. A. 2010. Integrin alpha4beta1 signaling is required for lymphangiogenesis and tumor metastasis. *Cancer Res.* 70(8):3042-51.
41. Alon, R., Feigelson, S. W., Manevich, E., et al. 2005. α4β1-dependent adhesion strengthening under mechanical strain is regulated by paxillin association with the α4-cytoplasmic domain. *J Cell Biol.* 171:1073-84.
42. Manevich, E., Grabovsky, V., Feigelson, S. W., Alon, R. 2007. Talin 1 and paxillin facilitate distinct steps in rapid VLA-4-mediated adhesion strengthening to vascular cell adhesion molecule 1. *J Biol Chem.* 282: 25338-48.

We claim:

1. A method for inhibiting monocyte and T-cell migration to inflammation sites in a pathological condition in a patient, said method comprising administering to said patient a composition comprising an effective amount of a compound of formula I

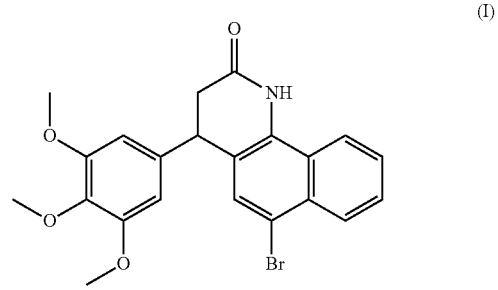 [SMILES: COc1cc(C2CC(=O)Nc3c2cc(Br)c2ccccc32)cc(OC)c1OC]

or a pharmaceutical acceptable salt or solvate thereof.

2. The method of claim 1 wherein the patient is selected from the group consisting of human, mammal, avian, fish and reptile species.

3. The method of claim 2 wherein the patient is human.

4. The method of claim 1 wherein said monocyte and T-cell migration to inflammation sites in a pathological condition results from an immune mediated disease selected from the group consisting of multiple sclerosis, asthma, inflammatory bowel disease, rheumatoid arthritis, diabetes mellitus type, I, systemic lupus erythematosus, Crohn's disease, vasculitis, familial Mediterranean fever, Behcet's disease, celiac disease, acute disseminated encephalomyelitis, Addison's disease; ankylosing spondylosis, aplastic anemia, autoimmune hepatitis, Graves' disease, Guillain-Barre syndrome, and Hashimoto's disease.

5. The method of claim 1 wherein the compound inhibits paxillin or a paralogue of paxillin from interacting with α4-integrin, and wherein the paralogue of paxillin is selected from the group consisting of leupaxin and Hic-5.

6. A method for blocking the α4 integrin-paxillin interaction in a condition selected from the group consisting of lymphangiogenesis and tumor metastasis comprising administering to a patient a composition comprising an effective amount of a compound of formula I

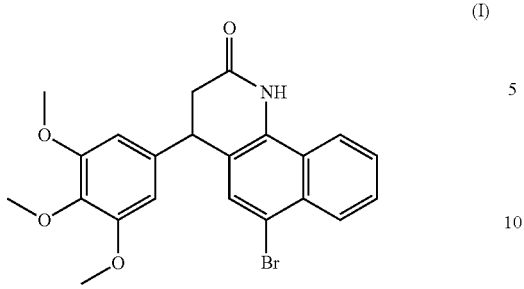
(I)

or a pharmaceutical acceptable salt or solvate thereof.

7. The method of claim 4 wherein the patient is selected from the group consisting of human, mammal, avian, fish and reptile species.

8. The method of claim 4 wherein the patient is human.

9. The method of claim 4 wherein the compound inhibits paxillin or a paralogue of paxillin from interacting with α4-integrin, and wherein the paralogue of paxillin is selected from the group consisting of leupaxin and Hic-5.

\* \* \* \* \*